United States Patent [19]

DeTore et al.

[11] Patent Number: 4,975,840
[45] Date of Patent: Dec. 4, 1990

[54] METHOD AND APPARATUS FOR EVALUATING A POTENTIALLY INSURABLE RISK

[75] Inventors: Arthur W. DeTore; Russell D. Suever; David W. Jones, Jr., all of Fort Wayne, Ind.

[73] Assignee: Lincoln National Risk Management, Inc., Fort Wayne, Ind.

[21] Appl. No.: 208,067

[22] Filed: Jun. 17, 1988

[51] Int. Cl.$^5$ .................. G06F 15/40; G06F 15/21
[52] U.S. Cl. ............................ 364/401; 364/408; 364/513
[58] Field of Search .................. 364/401, 408, 513

[56] References Cited

U.S. PATENT DOCUMENTS

| | | | |
|---|---|---|---|
| 4,346,442 | 8/1982 | Musmanno | 364/408 |
| 4,376,978 | 3/1983 | Musmanno | 364/408 |
| 4,591,983 | 5/1986 | Bennett et al. | 364/403 |
| 4,595,982 | 6/1986 | Burt | 364/300 |
| 4,597,046 | 6/1986 | Musmanno et al. | 364/408 |
| 4,622,013 | 11/1986 | Cerchio | 434/118 |
| 4,642,768 | 2/1987 | Roberts | 364/408 |
| 4,648,044 | 3/1987 | Hardy et al. | 364/513 |
| 4,658,370 | 4/1987 | Erman et al. | 364/513 |
| 4,674,044 | 6/1987 | Kalmus et al. | 364/408 |
| 4,722,055 | 1/1988 | Roberts | 364/408 |
| 4,766,539 | 8/1988 | Fox | 364/408 |
| 4,831,526 | 5/1989 | Luchs et al. | 364/408 |

OTHER PUBLICATIONS

Other Documents: Non-Confidential Exhibits 1-5 Confidential Exhibits 6-14.

Primary Examiner—Jerry Smith
Assistant Examiner—Kimthanh Tbui
Attorney, Agent, or Firm—Barnes & Thornburg

[57] ABSTRACT

A method and apparatus for evaluating the insurability of a potentially insurable risk has data bases for storing information, and the ability to correlate selected elements of information in respective data bases. Certain elements are assigned weights on the basis of predetermined relationships existing between elements of information in one data base and corresponding elements of information in another. Information is displayed from a data base for use by an underwriter in assigning a weight to a selected element, or an expert module corresponding to the selected element is identified and used for assigning the weight. A risk classification is determined for the potentially insurable risk from the weights assigned. The system can identify additional elements of information required for evaluating the potentially insurable risk, and can request entry of such information for subsequent storage. In one embodiment, the system can identify an element of information for which no corresponding information exists, and for which no expert module exists. Other features include the ability to override an expert module and assign a different weight to an element of information, the use of statistical profiles to adjust assigned weights, the ability to determine expected profitably resulting from decisions concerning a particular risk, and the provision of additional data bases useful in managing workload and customizing operation of the system.

42 Claims, 10 Drawing Sheets

METHOD AND APPARATUS FOR EVALUATING A POTENTIALLY INSURABLE RISK

BACKGROUND AND SUMMARY OF THE INVENTION

This invention relates to information processing apparatus and methods for evaluating the insurability of a potentially insurable risk.

Risk has been defined as the possibility of loss or injury. It is an element of every day life that cannot be avoided. Possible losses can take many forms, including: loss of life, health, property, or finances. Because it is not known when a particular loss will occur, and because the consequences of such loss can be very severe, people have learned to try to protect themselves from risks. Although there are several ways to do this, insurance is perhaps the most common. Insurance is designed to protect people and property from potential losses or injury. However, not all risks are insurable. For a risk to be insurable, the element of chance must be present, i.e., the loss should be caused by an uncertain future event which is not intentionally caused. The ability to evaluate the elements of chance and probability in determining the insurability of a potentially insurable risk is a complex process. In the past, individuals have assessed these risks from their own experiences supported by the accumulated experiences of the group with whom they work. Such individuals have been called underwriters, since they are willing to accept or underwrite a particular risk.

Today, there are many types of potentially insurable risks. Lives and health are at risk from infections, accidents, cancers, stress, heart disease, and other causes. Property is at risk from environmental sources such as fires and storms as well as from accidents, theft and vandalism. Further, protection from legal liability is an important and emerging issue. As society has changed, and the nature and number of potential losses have increased, the task of evaluating the insurability of potentially insurable risks has become more complex and demanding, and typically involves the review of more information than in the past. Due to these factors, and the variations in the abilities of individuals to assess the chance elements and probabilities associated with risks, and the financial consequences of poor decisions, there exists a need for improving the overall processes of evaluating risks by increasing access to information as well as coordinating and processing information from multiple sources. A need also exists for improving the manner in which the management of large organizations involved in the evaluation of risk (such as large insurance companies) implement policies concerning such evaluations.

An object of the present invention is to provide a method and apparatus for evaluating the insurability of a potentially insurable risk in an improved and more consistent manner.

This and other objects are attained in information processing methods and apparatus which provide first and second data bases; means for storing information relating to the subject risk in the first data base; means for identifying additional elements of information required for evaluating the risk, and means for requesting entry of the additional information for storage in the first data base; means for correlating elements of information from the first data base with corresponding elements of information in the second data base; means for assigning a weight to one of the selected elements of information from the first data base on the basis of predetermined relationships existing between information in the first data base and corresponding information in the second data base; means for displaying information from the second data base, corresponding to one of the selected elements of information from the first data base, for use in assigning a weight to that element of information, means for monitoring an input device for entry of the weight, and means for storing the weight following entry thereof; and means for determining a risk classification from the weights assigned to the elements of information in the first data base. In preferred embodiments, the methods and apparatus of the present invention further include a plurality of expert modules, and means for identifying an expert module corresponding to an element of information in the first data base for use in assigning a weight to that element of information. Provisions are also made for identifying elements of information in the first data base for which no corresponding information in the second data base exists and for which no expert module exists, and for selectively providing an option to assign a weight to such elements.

Other aspects of the present invention, which may also be incorporated into embodiments of the invention, include the ability to override the expert modules and to assign a different weight to the element of information, and to adjust the assigned weights on the basis of statistical profiles relating to the subject information.

In certain embodiments of the invention, the risk classification is determined by combining the weights assigned to the elements of information in the first data base to derive a single weight representative of the subject risk. This single weight is then compared to a standard for a risk of the same class, and a conversion is performed to arrive at the proper risk classification. The method and apparatus of the present invention preferably allows for determination of an expected profit which may result from a decision based on the risk classification, determination of the probability of generating such a profit, and the impact on the expected profit of changing the risk classification.

Certain embodiments of the methods and apparatus of the present invention include a user data base, an installation specific data base, and a management information data base. The user data base is useful for storing information relating to a plurality of system users, and for selecting one of the users for subsequent identification with the potentially insurable risk to be evaluated. Users are selected on the basis of training, experience, workload, and any of a number of marketing factors. The installation specific data base is used for storing information which may be specific or peculiar to a particular site, geographical location, marketing group, or other designated category, and for factoring such specific information into the assigning of weights to the elements of information in the first data base. The management information data base allows the method and apparatus of the present invention to be monitored and modified, as deemed appropriate.

Other objects, advantages and novel features of the present invention will become apparent from the following detailed description of the invention when considered in conjunction with the accompanying drawings.

DETAILED DESCRIPTION OF THE DRAWINGS

Before discussing the preferred embodiment of the invention which is described and illustrated in FIGS. 1-12, it should be noted that, although the invention will be discussed in terms of its applicability to the evaluation of risks inherent in underwriting life insurance, the broader aspects of the invention are not necessarily limited to this particular application. Although the preferred embodiment of the invention described below does offer particular advantages in the field of life and health insurance, it is felt that adaptation and application of the invention to other fields, such as the underwriting of property and casualty insurance risks, will also be advantageous. Accordingly, the scope of the invention is not intended to be limited by the details of the preferred embodiment discussed below, but rather by the terms of the claims following this detailed description. It should also be noted that, although terms of art such as "underwrite," "underwriter," "policy," etc. are used throughout the following discussion, these terms are not intended to unduly limit the applicability of the system of the present invention. For example, although a life insurance "underwriter" (as defined by today's industry standards) will most surely benefit from the system described below, it is likely that others not presently designated as "underwriters" will be able to use and benefit from the invention and, accordingly, may be considered "underwriters" for purposes of this application.

Figure 1:
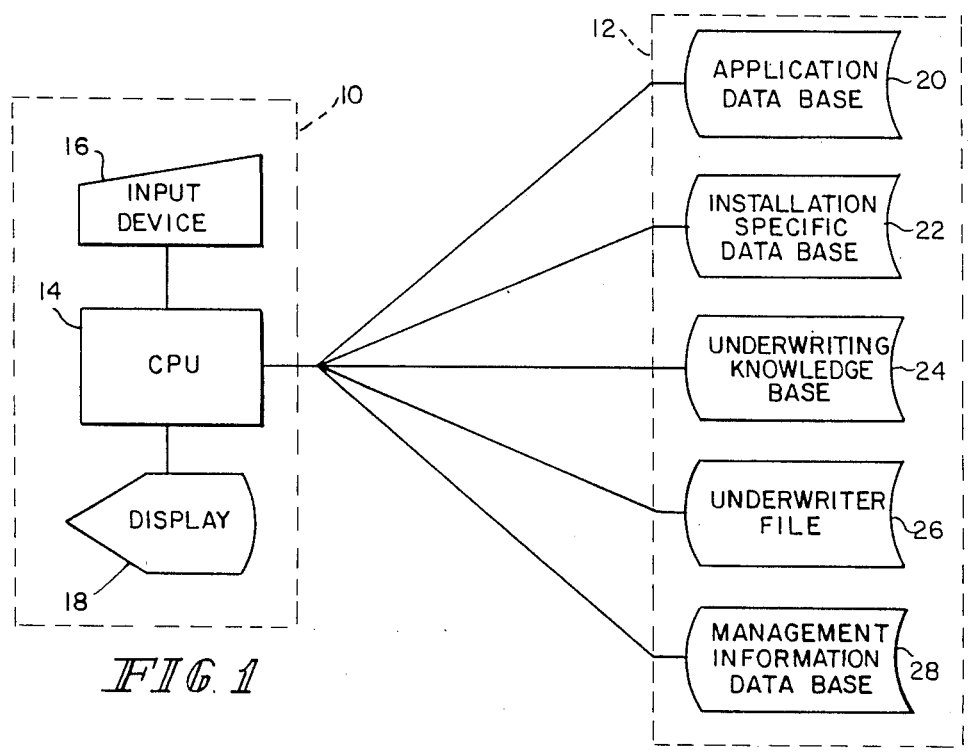
FIG. 1 shows a block diagram of a generalized computer system suitable for use in practicing the present invention.

FIG. 1 shows a generalized computer system suitable for use in practicing the present invention. The system includes a terminal 10 and a memory unit 12. Terminal 10 comprises a central processing unit (CPU) 14, an input device 16 which may, for example, be a keyboard, and a display 18 which may be a standard cathode ray tube monitor Memory 12 may be constructed integrally with terminal 10 or, alternatively, may be located remotely from terminal 10 and accessed via telephone or other communication lines. Computers suitable for use in practicing this invention include personal computers (such as an IBM Personal System-2, Model 80), other micro-computers, mini-computers, mainframe computers, or networks or combinations of any of the above.

For purposes of this discussion, memory 12 can be visualized as being divided into a number of data bases, knowledge bases and files, as illustrated. In practice, these divisions may be reflected in the physical structure of memory 12 by providing a plurality of separate memory devices corresponding to the divisions illustrated. Alternatively, a single memory device containing all the stored information necessary for practice of the invention may be used. In the discussion which follows, the data bases, knowledge base, and file illustrated in FIG. 1 will be discussed as separate entities by way of example and illustration only.

Memory 12 includes application data base 20, installation specific data base 22, underwriting knowledge base 24, underwriter file 26 and management information data base 28. Application data base 20 contains all information collected from the applicant or applicants, including personal data (age, address, occupation, avocations, income level, etc.), medical information (prior medical problems, existing conditions, medications, etc.), and any other information received from the applicant which may have a bearing on insurability. In addition, application data base 20 may contain the results of medical tests and examinations, inspection reports, medical histories, and other information provided by third parties bearing on the question of insurability of the applicant.

Installation specific data base 22 contains rules, guidelines, procedures, and other information for use in evaluating the information in data base 20 which are specific to a particular company, location, or site. Although many of the rules and much of the information used in evaluating risks tend to be generic in their application, the existence of data base 22 does provide for some degree of customization of the system. Information in data base 22 may be modified as necessary or desired to allow for a degree of product differentiation in the underwriting process. Files of installation specific variables within data base 22 which may be subject to modification include, but are not limited to, age and amount limits for ordering examinations, levels for inspection reports, and levels for blood test workups. These variables are set at the time of system installation, and may be modified at any time to reflect changes in product design or the offering of new products.

Figure 8:
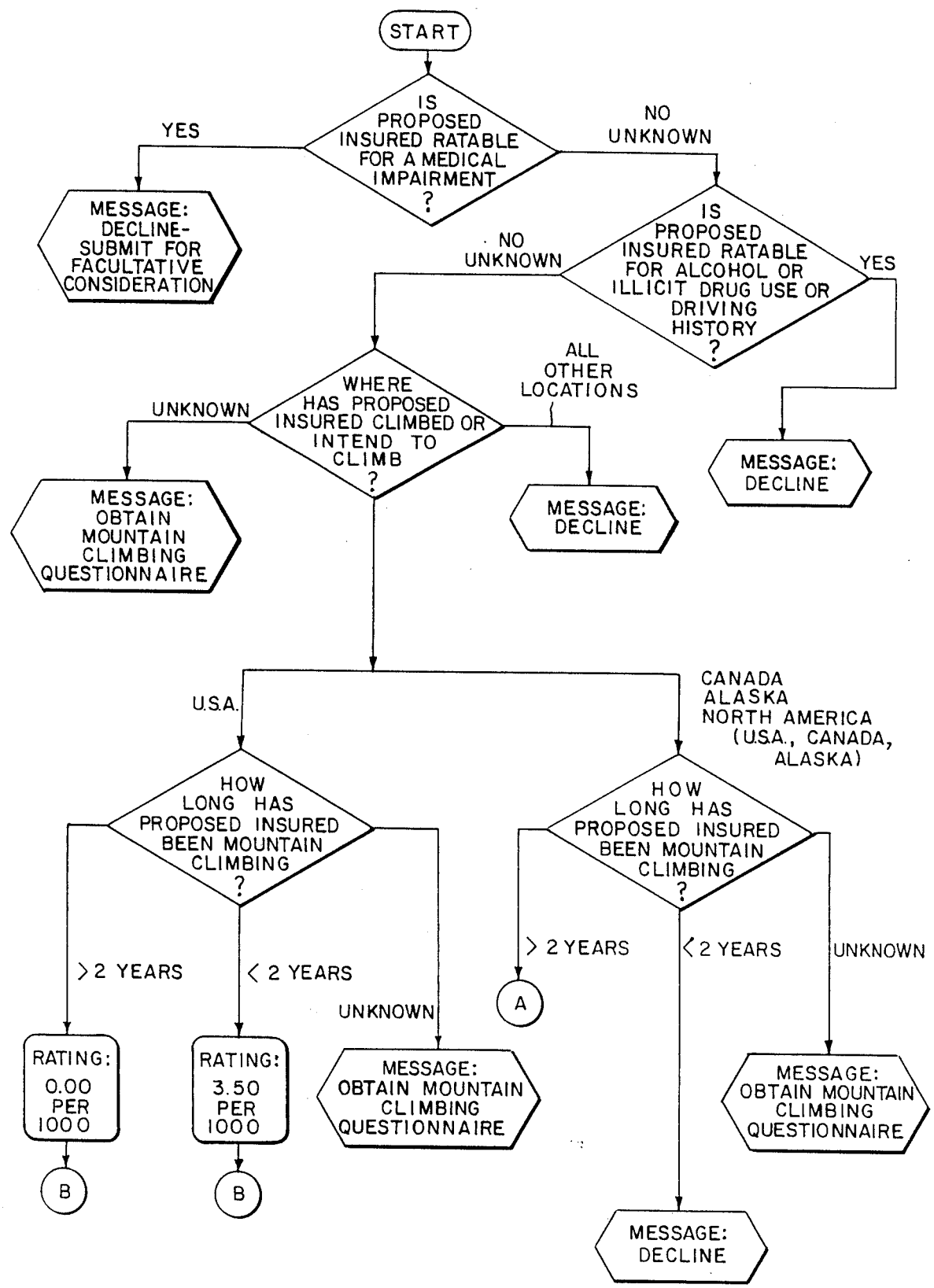
FIGS. 8-10 show flow charts which illustrate the workings of an exemplary expert module in the form of an expert system, of the type used in conjunction with the present invention.
Figure 9:
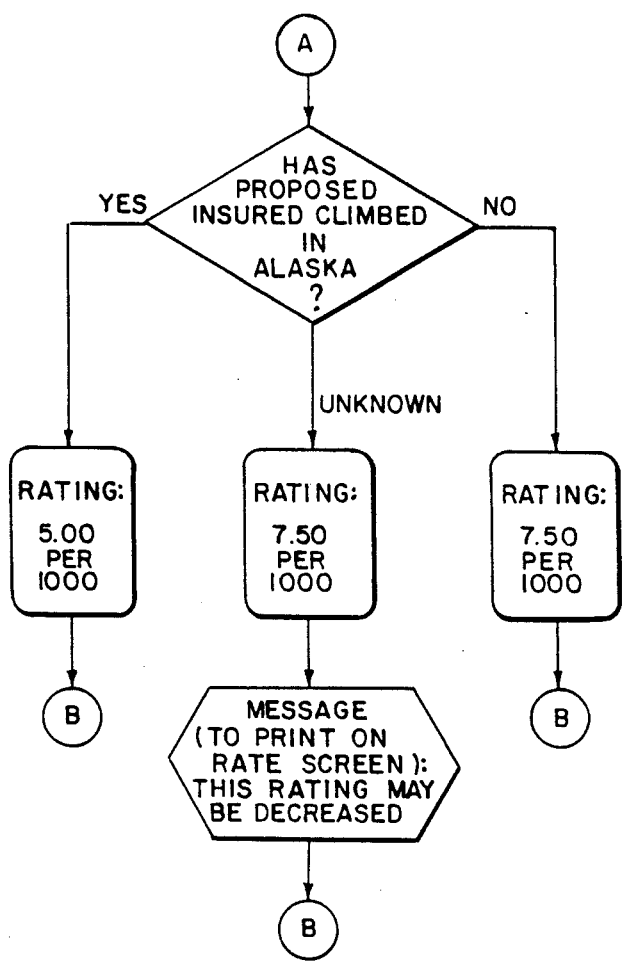
Figure 10:
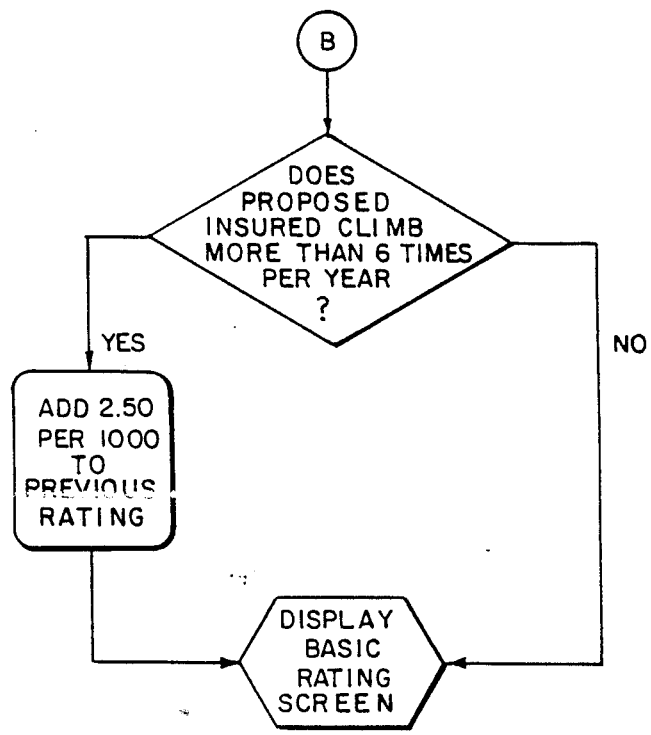

Underwriting knowledge base 24 is the information base that drives the system. It incorporates the copyrighted information contained in the underwriting manuals used by the assignee of the present invention. Underwriting knowledge base 24 is divided into textual elements that describe the underwriting process, factual elements on specific medical conditions or impairments impacting upon mortality, and programmed knowledge, in the form of expert modules, which expertly direct the system user through the underwriting process for selected problems or impairments. Examples of the information related to specific impairments (e.g., blood pressure—hypertension and build) which are included in knowledge base 24 are attached to this specification as Appendix A. An example of the programmed knowledge base, or expert modules, which are included in knowledge base 24 is illustrated in FIGS. 8-10 which are discussed in detail below.

The programmed knowledge base is interwoven with the textual information so as to allow the text to be used to provide explanations for the programmed decisions reached by the expert modules. It should be noted that the term "expert module", as used in this application, includes the type of deductive programming illustrated in FIGS. 8-10 and commonly referred to as an expert system. However, the term "expert module" is not intended to be limited to this particular type of programming or technique of analysis. An expert module may include a regression analysis, a discriminate function, loglinear analysis, linear programming, or any other technique which may be used by experts in analyzing and evaluating the risks associated with a particular problem or situation.

Figure 2:
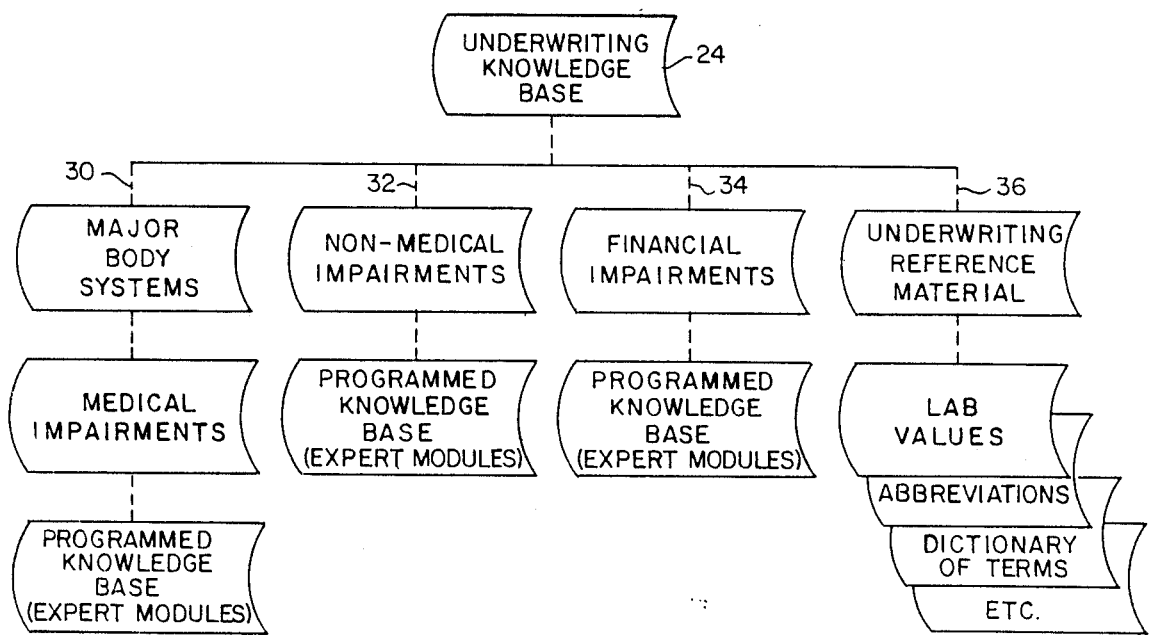
FIG. 2 shows a block diagram which illustrates the logical organization of the underwriting knowledge base as used in a preferred embodiment of the invention which relates to evaluating risks associated with life insurance.

Underwriting knowledge base 24 is logically organized as illustrated in FIG. 2. Underwriting knowledge base 24 includes, on a first "branch" 30, information on each major body system and various medical impairments associated therewith. Branch 30 further includes a programmed knowledge base which includes one or more expert modules relating to medical conditions (e.g., asthma) which are used in analyzing information provided from application data base 20, installation specific data base 22, or other parts of memory 12. Branch 32 includes non-medical text material explaining the underwriting approach used in connection with non-medical impairments (e.g., avocations, such as mountain climbing), along with the associated expert modules (see, for example, FIGS. 8-10). Branch 34 includes information relating to financial considerations, and the expert modules associated therewith. Branch 36 includes additional underwriting reference materials (e.g., laboratory values, abbreviations, a dictionary of medical terms, etc.) in readily available form for the user.

For purposes of this discussion, the term "problem" will generally mean an element of information (e.g., facts and conditions such as age, a medical condition, a hazardous avocation, a smoking or drinking habit, etc.) stored in application data base 20 which impacts either positively or negatively upon the relative mortality of the proposed insured. The term "impairment" will generally mean an element of information (e.g., the impacts of aging, various medical conditions, avocations, smoking, drinking, etc. on the mortality of known populations) stored in underwriting knowledge base 24 which relates to or corresponds with the information contained in application data base 20. Each impairment is associated with textual information and/or an expert system or module which is intended to assist the system operator in quantifying the impact of a particular problem (by reference to a corresponding impairment) upon expected mortality in a particular instance. In broad terms, the approach to evaluating or underwriting a given risk which is incorporated into the process of the present invention includes the following steps:

1. Identifying a problem from the information contained in application data base 20;
2. Matching or correlating the identified problem with a corresponding impairment from underwriting data base 24;
3. Assigning weights (i.e., debits or credits) to the identified problems on the basis of information contained in the underwriting data base; and
4. Determining a risk classification for the given risk by combining the assigned weights.

As will be seen from the discussion which follows, the system of the present invention is capable of completing this process without the aid or intervention of skilled underwriters or other personnel in some cases and, in more difficult cases, is helpful in improving the efficiency, quality, and consistency of decisions which do require input from skilled underwriters.

Referring again to FIG. 2, the system of the present invention allows the user to reference any of the textual material contained in underwriting knowledge base 24 in a non-underwriting mode (i.e., the underwriter need not be underwriting a case to reference the material). The programmed knowledge bases, or expert modules, can be executed in a non-underwriting mode as well. With a minimum amount of input data, a test case may be processed through execution of the expert modules. This non-underwriting mode of referencing the system is especially useful in training or "what-if" modes of system operation.

Memory 12 also includes underwriter file 26. File 26 includes background information on available underwriters, including level of experience or skill, geographical location, current workload, and other factors which might influence the assignment of cases to a particular underwriter. Memory 12 further includes management information data base 28. Data base 28 stores information relating to usage of the system of the present invention, including information relating to the number of cases evaluated by system users, the time required to evaluate each case, and other items of information from which determinations as to the effective uses of the system can be reached. This feature of the invention is discussed in further detail below.

Figure 3:
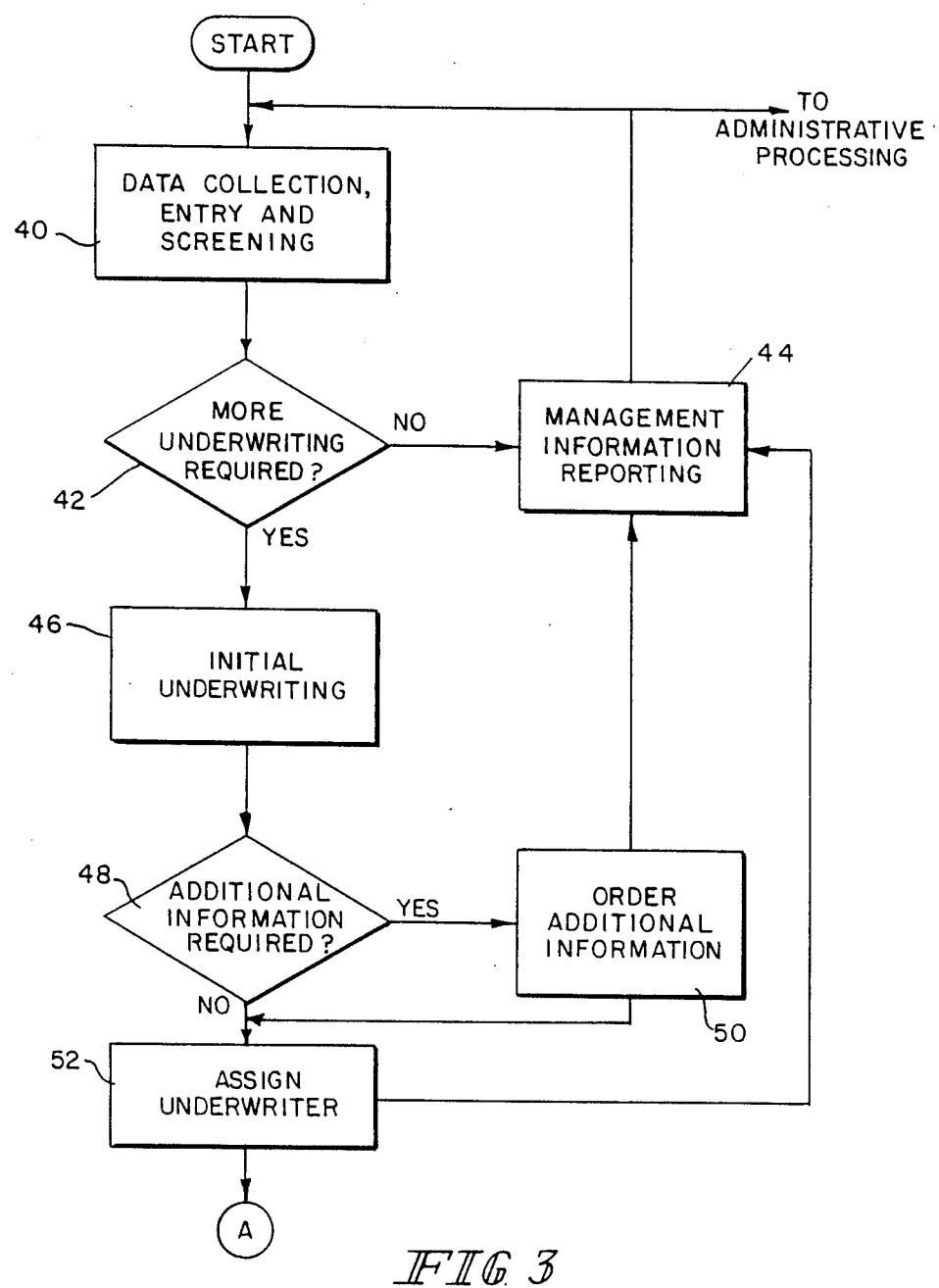
FIG. 3 shows a flow chart which illustrates data collection, entry, and screening, and initial underwriting features of the present invention.

FIGS. 3-7 show flow charts which illustrate the basic operation of the system of the present invention. Referring specifically to FIG. 3, block 40 represents the initial step of data collection, entry, and screening. In this step, a basic amount of data on each case is collected and simple screening is performed, preferably concurrently with data collection. Data may be collected by having an applicant complete an application form, with the information subsequently entered into the system by a keyboard operator. Alternatively, an applicant, or an applicant's agent or representative, may enter information directly from a keyboard or other input device. It is specifically contemplated that, at this stage of the process, a skilled underwriter would not be required or involved. It is also contemplated that initial data collection and screening may be performed to some degree outside the system, with some version of the results and information subsequently entered into the system if necessary. It is also noted that these initial steps normally require significant customization on a company-by-company basis, beyond the customization which ca be achieved through changes in the installation specific data base.

As noted initial screening of the information preferably takes place concurrently with information collection. Initial screening allows for decisions to be made regarding a certain percentage of the incoming cases. Currently, life insurance studies have shown that five to nine percent of the incoming cases are "clean" cases which can be disposed of (i.e., by issuing or declining to issue coverage) on the basis of the initial screening process. The percentage of cases which may be dealt with on this basis varies as the characteristics of the product (i.e., type of policy, amount of coverage requested, etc.) and the nature of the companies' business vary.

After initial data collection, screening and entry, the system determines whether or not additional underwriting is required. This step is represented by block 42. If no additional underwriting is required, appropriate entries in management information data base 28 are made in a management information reporting step, generally represented by block 44 of FIG. 3. The information reported and stored in this step allows for evaluation of how efficiently the system deals with various types of cases and provides a statistical base from which improvements and refinements in the system can be made. Use of this information may be made internally (for example, to automatically change or update the installation data base) or, alternatively, the information may be transferred out of the system for external administrative processing. In addition to allowing for modification of the system, the information collected in the reporting step provides administrators and management with trend information which may be useful in strategic decision making.

If the system determines that more underwriting is required for a particular case, the program proceeds to the initial underwriting step which is generally represented in FIG. 3 by block 46. Initial underwriting analyzes cases by considering financial, medical and non-medical factors, or "impairments" and their interactions to define underwriting problems requiring further underwriting action. Initial underwriting also determines if additional information is required to underwrite a particular case (decision block 48) and, if so, preferably generates requests for the additional information (block 50). Such additional information and requirements may include (without limitation) medical examinations, test reports, financial statements, and public records (e.g., motor vehicle reports).

The financial element of initial underwriting preferably establishes or evaluates a number of items, such as the following:
a. the age group of the proposed insured (e.g., juvenile, young adult, adult, elderly);
b. the employment status of the proposed insured;
c. the insurable interest of the proposed beneficiary;
d. the relationship of the proposed policy owner to the proposed insured;
e. the purpose of the insurance (e.g., personal, charity, business related, etc.); and
f. the appropriateness of additional benefits, such as accidental death benefits, waiver of premiums and guaranteed insurability riders.

In addition, the financial element defines financial problems in terms of the financial information contained in underwriting knowledge base 24, and identifies any additional financial information or data required for further underwriting action.

The non-medical element of initial underwriting preferably:
a. identifies non-medical problems from the information in application data base 20 and defines the nature of the non-medical problems;
b. determines the weights (debits or credits) associated with the non-medical problems using data from application data base 20 correlated to the non-medical information contained in underwriting knowledge base 24;
c. identifies non-medical problems requiring additional underwriting action which must be subsequently addressed by an underwriter; and
d. identifies any additional information required if further non-medical underwriting action is merited and preferably generates requests for the additional information.

The medical element of initial underwriting will preferably:
a. define medical problems from the applicant's health complaints, symptoms, use of medications, history of medical consultations, surgeries, tests, etc.;
b. define medical problems from the applicant's medical history or family history of specified illnesses;
c. classify the severity of medical problems according to severity groups;
d. evaluate basic medical test results for the existence of possible health problems (e.g., evaluate ECG, blood pressure, heart rate, blood tests, urine nicotine, etc.);
e. determine the need for further medical information from the severity of the medical problems defined, the applicant's age, timing of the problems, amounts of coverage requested, etc.;
f. establish links or matches, if possible, between the medical problems identified and specific impairments in underwriting knowledge base 24; Note—establishment of a proper match cannot always be done automatically by the system in the initial underwriting step, and may require underwriter intervention later in the process, as will be discussed more fully below;
g. determine the weights to be assigned to the medical problems which are successfully matched to medical impairments in underwriting knowledge base 24; and
h. identify, and preferably request, additional information required for further medical underwriting.

The financial, non-medical, and medical problems (and their interrelationships) identified as requiring additional underwriting action in the initial underwriting step are stored for further action by a skilled underwriter. In addition, any problems which are identified, but which are not classifiable as financial, non-medical, or medical problems, will also be stored for further attention by the underwriter.

When it has been established that additional underwriting is required (i.e., at least some problems remain unresolved after the initial screening step), and initial underwriting has occurred to further define the problems and to identify and request any additional information which may be required to resolve the problems, the case is assigned to an underwriter for resolution. This step is represented by block 52 in FIG. 3. Cases are assigned to an underwriter on the basis of underwriter availability (e.g., cases are not assigned to an underwriter who is on vacation), level of experience or skill, workload, and any of a number of marketing factors, such as geographical or office location of the underwriter, type of product (policy) requested, and amount of policy. Once assigned, the case will appear in the "in tray" of the designated underwriter. The "in tray" refers to a list of cases within the system which are awaiting underwriting action by the selected underwriter.

Following assignment of the underwriter, the system stores relevant information (e.g., the identity of the selected underwriter and information concerning the status of the case) in the management information data base (block 44).

Figure 4:
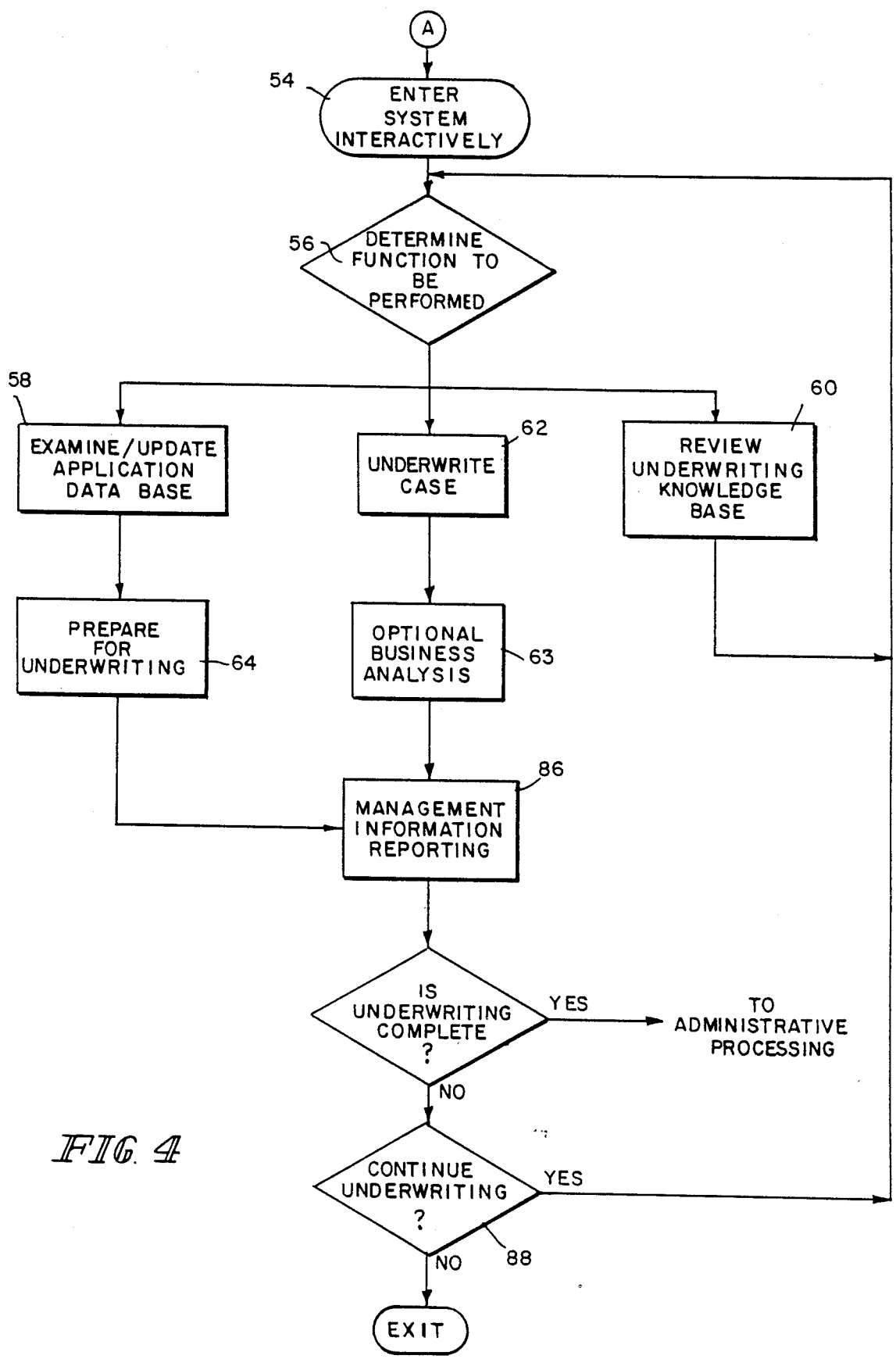
FIG. 4 shows a flow chart which illustrates the complex underwriting feature of the present invention.

FIG. 4 shows a flow chart which illustrates the process of resolving or underwriting the problems identified in the course of initial underwriting. After a case has been assigned to a designated underwriter, in accordance with the above discussion relating to FIG. 3, and the selected underwriter logs onto the system (after entering the appropriate password and satisfying other applicable security measures), the underwriter selects a case to be underwritten. This procedure is generally represented by block 54 in FIG. 4. It is presently contemplated that the underwriter to which cases will be assigned by the system is a relatively highly skilled individual, and is not likely to be the same individual who will operate the system through the data collection, screening and entry process and through initial underwriting. However, in certain circumstances, it may be useful or desirable for a single individual, having the requisite level of skill, to complete the entire process as illustrated in both FIGS. 3 and 4. It should also be clearly understood that use of the term "underwriter" in this application does not necessarily restrict the use or value of the present system to those presently recognized as "underwriters" in the insurance industry of today. While such individuals will surely benefit from the present system, the benefits and advantages offered by the system in the underwriting process may very well expand or otherwise change the current definition of the term "underwriter" such that individuals who would not necessarily be deemed underwriters in the present industry may be able to function in an underwriting capacity with the aid of the present system. Accordingly, use of the term "underwriter" in the present application should not be construed to be limiting in any way to the applicability or scope of the present invention.

After logging on to the system, the selected underwriter is greeted by a menu of options which preferably include the following system capabilities:

1. Examine or update application data base 20;
2. Review underwriting knowledge base 24;
3. Underwrite the case.

The process of selecting the desired option is represented by block 56 of FIG. 4, and the individual options listed are represented by blocks 58, 60 and 62, respectively.

With reference to block 58 of FIG. 4, application data base 20 contains all of the elements of information relating to the potentially insurable risk which are necessary to underwrite the case. The underwriter is allowed to examine and review the information in application data base 20, and has the capability of updating the information as necessary for further underwriting of the case. These capabilities are used to continually update a case as new or expanded information is received. Upon reviewing the information in application data base 20 relating to the subject case, the assigned underwriter may elect to transfer the case to other consulting underwriters or medical directors. If this option is exercised, the case responsibility is transferred to the receiving underwriter/ medical director for disposition or reassignment, and the management information data base is subsequently updated accordingly.

Figure 5:
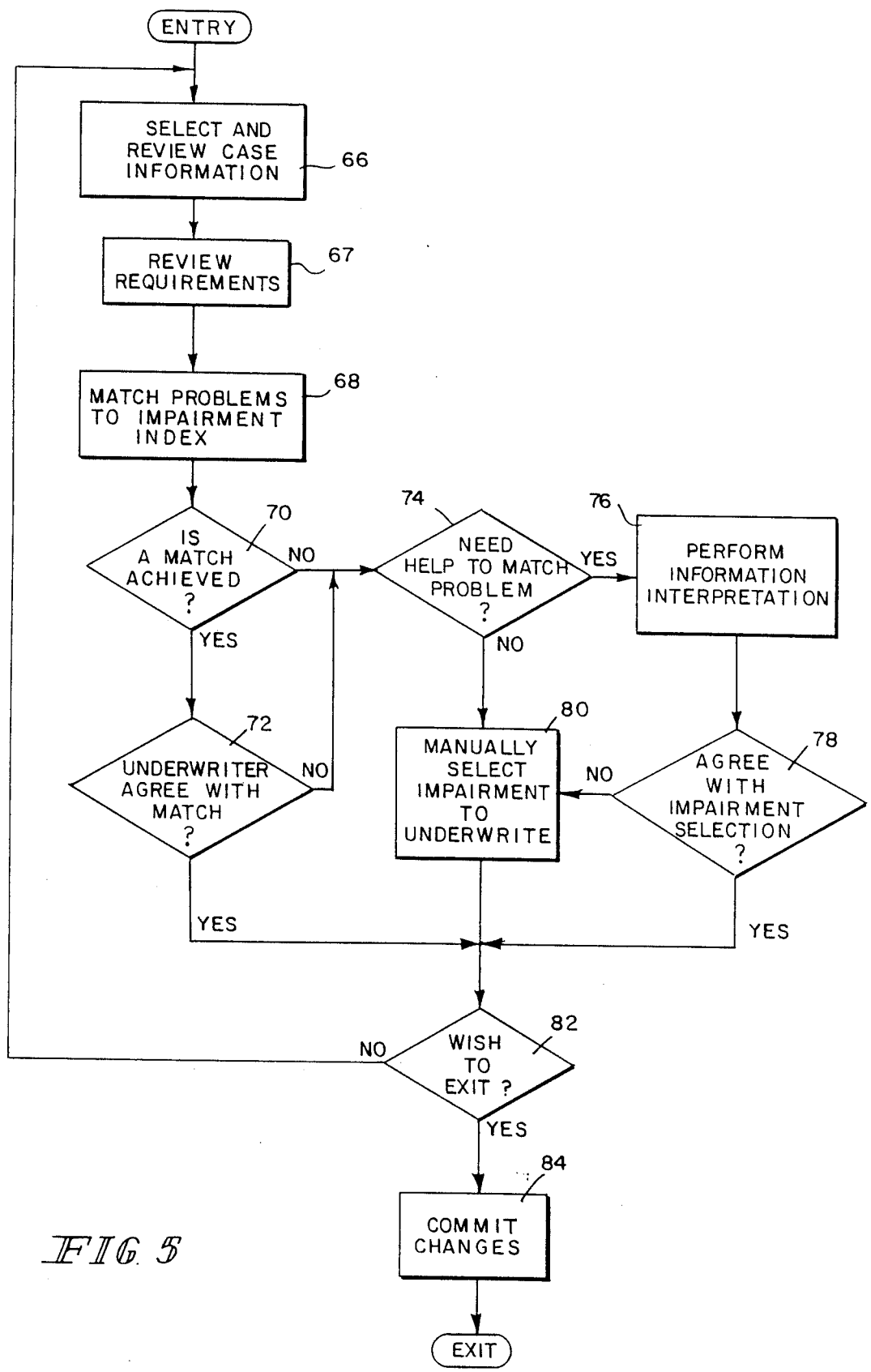
FIG. 5 shows a flow chart which illustrates the process of preparing for underwriting in the system of the present invention.

Once the decision has been made to underwrite a case, the underwriter prepares by first selecting the case to be underwritten from the "in tray" of cases awaiting underwriting action. These cases have basic identification information that will allow the underwriter to prioritize the assigned workload for a given period of time. After examining or updating application data base 20, the underwriter proceeds, if necessary, through the process of preparing for actual underwriting, which is generally represented by block 64 in FIG. 4. The process represented by block 64 is illustrated as a separate subroutine in FIG. 5. With reference to FIG. 5, the selected case is first displayed for underwriter review of the application data, the problems identified by the initial underwriting process, and the additional requirements or information requested or recommended by initial underwriting. This process is represented by block 66 in FIG. 5.

As a separate step in the process at this point, the system provides for a review by the underwriter of the applicable requirements (block 67). As used herein, the term "requirements" means those elements of information such as electrocardiograms, blood test and urinalysis results, medical records, financial statements, consumer investigative reports, motor vehicle reports, and other relevant information not available from the application data which should normally be considered to come to a decision regarding the underwriting of a particular problem. In addition to reviewing applicable requirements relating to the case at hand, the underwriter is given the opportunity to waive certain requirements or to request additional requirements as deemed appropriate for the particular case, and as allowed by the system.

The system will attempt to match or correlate the problems in application data base 20 with specific impairments listed in an impairment index of underwriting knowledge base 24 (block 68). This will normally be achieved if there is an exact match of the problem description in application data base 20 with an impairment in the impairment index of underwriting knowledge base 24. Examples of problems in application data base 20 which may be identified by the system and matched to impairments in the impairment index of underwriting knowledge base 24 are:

| Problem | Impairment |
| --- | --- |
| 1. Heart Attack | Myocardial Infection |
| 2. Blood Pressure | Blood Pressure |
| 3. Duodenal Ulcer | Peptic Ulcer Disease |
| 4. Kidney Stone | Stones (Calculi) Urinary Tract |
| 5. Syphilis | Sexually Transmitted Diseases |
| 6. Arthritis | Arthritis |
| 7. Depression | Affective Disorders |
| 8. Seizure Disorder | Epilepsy |
| 9. Scuba Diving | Scuba Diving |
| 10. Motorcycle Racing | Vehicle Racing |

If all problems identified have been successfully matched to an impairment (block 70) and the underwriter agrees (block 72) with the match designated by the system, processing may continue. If a match is not achieved, or if a match is achieved but the underwriter disagrees with the match, the underwriter may proceed in one of two ways, as represented by decision block 74. First, if the underwriter does not know or is unsure of what impairment to underwrite, and needs help in matching the subject problem to an impairment in the impairment index, the underwriter may initiate an information interpretation process (block 76). This process may itself be an expert module whose purpose is to evaluate the information contained in application data base 20, determine the specific impairment to underwrite for a particular problem (e.g., a medical abnormality identified in the application or a subsequent medical exam), and guide the underwriter to the appropriate expert module or section of underwriting data base 24 to underwrite that impairment. In this process, basic applicant data such as sex, age, height, weight, and the subject problem or impairment are combined with other data from underwriting knowledge base 24, such as symptoms, medical problems, medications used for particular impairments, laboratory test standards, other related impairments, and primary body functions affected. This information is evaluated by the information interpretation expert module which functions in the same manner as an expert diagnostic tool and is based on expertise which would normally be available only from highly skilled professionals. After evaluating this information, the information interpretation expert module makes a recommendation as to the most likely impairment(s) to underwrite. The underwriter is then prompted for agreement or disagreement with the subject recommendations (block 78).

If the underwriter does not agree with the selection of impairments recommended by the information interpretation expert module, or if the underwriter feels that a proper match can be achieved without the aid of information interpretation, the underwriter is given an opportunity to manually select an impairment from the impairment index (block 80). This manual selection process may be facilitated by providing the underwriter with the ability to perform a key word or partial key word search of the impairment index. In any event, it is not required that the system or the underwriter achieve a match between each problem identified and an impairment in the impairment index. Two possible outcomes result from an inability to achieve a match:
  a. the problem/impairment is relatively obscure and does not exist in underwriting knowledge base 24. In this case, the impairment is identified as not being in underwriting knowledge base 24 which indicates to the system that this problem will be underwritten from the experience of underwriter without the benefit of information from underwriting knowledge base 24; or
  b. the problem/impairment is left unmatched until additional information is obtained. In this case, a final underwriting action cannot be reached without the additional information. However, the underwriting process is allowed to proceed for all matched problems/impairments, without regard to the unmatched problems/impairments. The unmatched problems/impairments may ultimately be referred to appropriately skilled personnel (e.g., the medical director) for special handling and evaluation.

At this point, the application is ready for actual underwriting. However, actual underwriting need not be done at this time. The underwriter is given the option to exit the subroutine illustrated in FIG. 5, or to proceed with selection and review of a different case (block 82). When a decision is made to exit the subroutine, the underwriter is prompted to affirmatively commit any changes made to application data base 20 (block 84). Upon exiting the subroutine of FIG. 5, the system optionally makes appropriate entries in the management information data base (block 86), and the underwriter may continue with the underwriting process (block 88).

The second of the options provided to the underwriter by the system illustrated by the flow chart of FIG. 4 is that of reviewing underwriting knowledge base 24 (block 60). As previously noted, the system of the present invention allows the underwriter to reference any of the textual material contained in underwriting knowledge base 24 for educational or training purposes, or for other reasons. The expert systems or modules within underwriting data base 24 can also be executed for whatever benefits the underwriter might derive therefrom.

Block 62 represents the third option provided to the underwriter. That option is to proceed with actual underwriting of a case. In the underwriting process as completed by the system of the present invention to this point, each problem in application data base 20 which was identified in initial underwriting will be matched (assuming that a match exists) to a corresponding impairment in underwriting knowledge base 24. Each impairment on underwriting knowledge base 24 is associated with textual information on the knowledge base which describes the underwriting process as it relates to that impairment. In addition, a particular impairment may have a programmed knowledge base or expert module associated therewith. The preferred system priority in completing the underwriting process is: (1) use an expert module, when available, to underwrite an impairment; (2) use the textual description of the underwriting process in the knowledge base to underwrite an impairment for which an expert module does not exist; and (3) allow the underwriter the option to underwrite an impairment for which neither an expert module nor a textual description of the underwriting process exists The third alternative should occur only when the impairment is obscure and is not documented on underwriting knowledge base 24.

Figure 6:
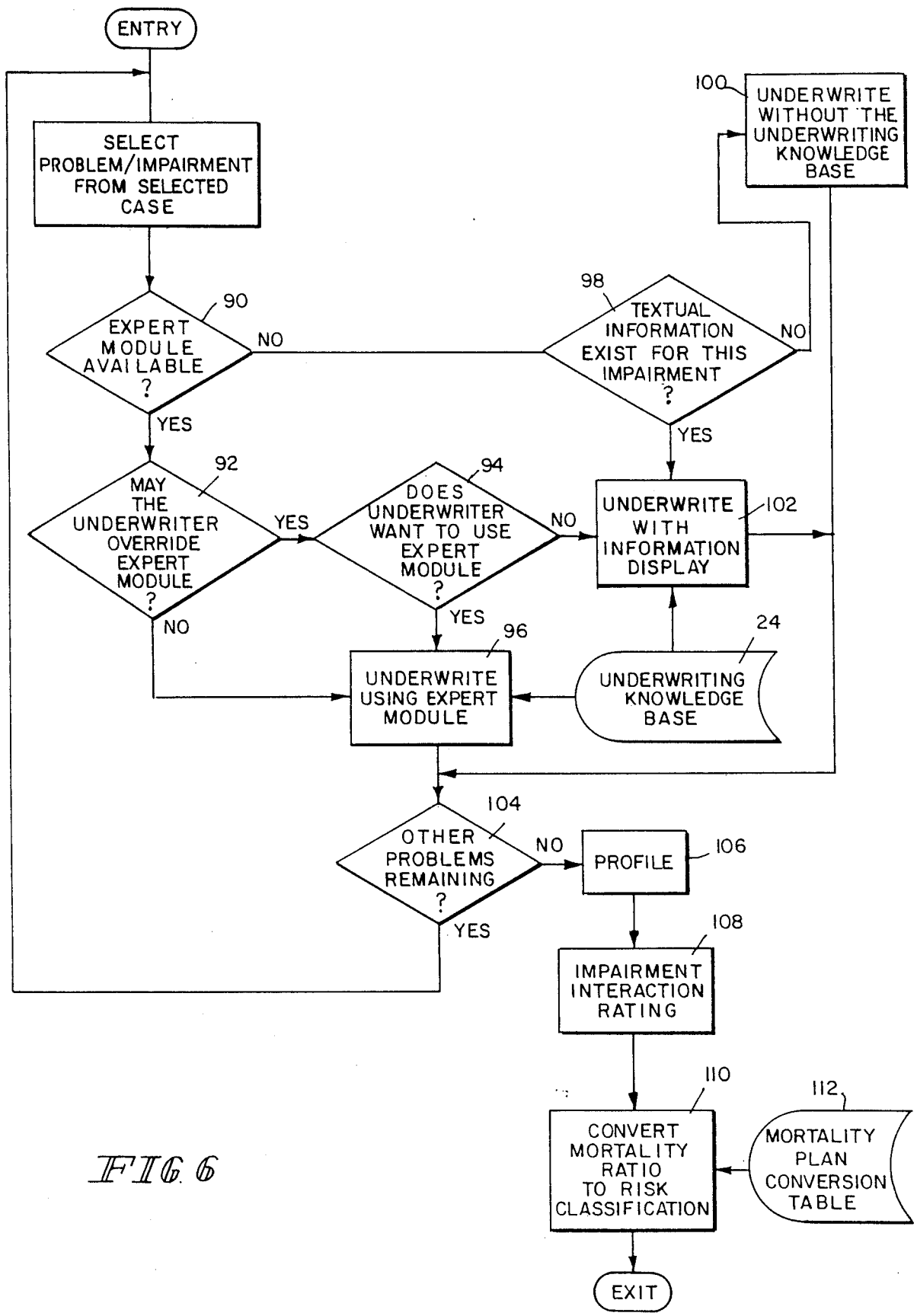
FIG. 6 shows a flow chart which illustrates the underwriting process of the present invention in additional detail.
Figure 7:
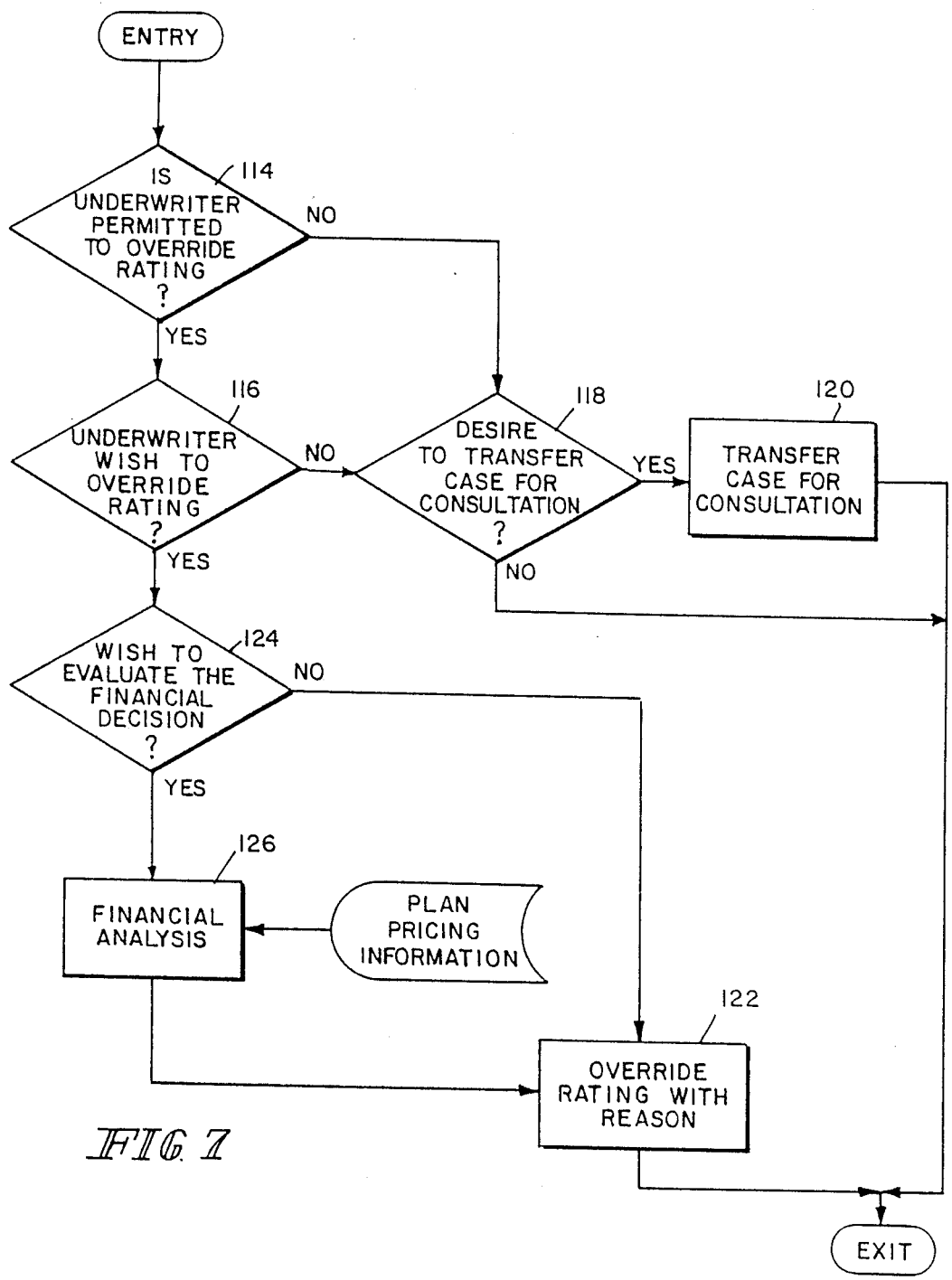
FIG. 7 shows a flow chart which illustrates the business analysis feature of the present invention in additional detail.

Referring now to FIG. 6, each problem in a particular case is considered on an individual basis. Underwriting knowledge base 24 is first checked for the existence of an expert module (block 90). If an expert module is available, it is used for underwriting the subject problem unless the underwriter is rated as an expert underwriter with regard to the subject problem, in which case the system provides the underwriter an option to override the expert module (block 92). If the underwriter cannot override the expert module, or if a qualified underwriter chooses to use the expert module to underwrite the problem (block 94), the system proceeds with underwriting using the expert module (block 96). For purposes of illustration, an expert module used when the initial underwriting process indicates that the applicant participates in mountain climbing activities is illustrated by the flow charts of FIGS. 8-10. Referring to FIG. 8, the expert module first determines whether the proposed insured is ratable for a medical impairment. If so, the system recommends that coverage be declined, pending submission of the case for special consideration. If the proposed insured is not ratable for a medical impairment, the system determines whether the proposed insured is ratable for alcohol or illicit drug use, or a relevant driving history. If so, the system recommends that coverage be declined. If not, the system inquires as to where the proposed insured intends to climb. If unknown, the system requests that this information be obtained via a mountain climbing questionnaire. If climbing is to be done in locations other than North America, coverage is declined If climbing is to be done in the U.S.A. only, the system inquires as to how long the proposed insured has been mountain climbing. If unknown, use of the mountain climbing questionnaire to obtain this information is recommended. If the proposed insured has been climbing for less than two years, a rating for mountain climbing of, for example, $3.50 per $1,000 requested coverage is recommended. If the proposed insured has been climbing for more than two years, no additional premium related to mountain climbing is required After making the latter two determinations, the system branches to FIG. 10 wherein it is determined if the proposed insured climbs more than six times per year. If not, the previously determined rating is displayed on the basic rating screen. If yes, an additional factor of $2.50 per $1,000 is added to the previous rating for mountain climbing, prior to display of the basic rating screen.

Referring back to FIG. 8, if the proposed insured intends to climb in Canada and Alaska, the system again determines how long the proposed insured has been mountain climbing. If unknown, this information is requested via the questionnaire. If less than two years, coverage is declined. If greater than two years, the program branches to FIG. 9, wherein it is determined if the proposed insured has climbed in Alaska. If unknown, a rating for mountain climbing of $7.50 per $1,000 is assigned and printed on the basic rating screen, along with a message indicating that this rating may be decreased pending receipt of the unknown information. If yes, a rating for mountain climbing of $5.00 per $1,000 is assigned. If no, a rating for mountain climbing of $7.50 per $1,000 is assigned. After assignment of each of these ratings, the program branches to the loop of FIG. 10 for final determination of the basic mountain climbing rating and display of the rating on the basic rating screen.

Similar, although usually more complex, expert modules exist for other medical and non-medical impairments in knowledge base 24. As illustrated by the system of FIGS. 8-10, the expert modules use programmed reasoning to determine the weights to be assigned to the subject problem. This approach allows even a relatively inexperienced underwriter to uniformly evaluate problems in a wide variety of areas, and to arrive at a determination as to how such problems should be treated in the underwriting process.

If an expert module does not exist but textual information for the subject impairment does exist, then the textual information on underwriting knowledge base 24 is preferably used by the underwriter in determining the weights to be assigned for a particular problem. When textual information on the subject impairment is not available, the underwriter will underwrite the problem in the same manner, except that no textual information will be available from the system for the underwriter's reference. The quality of ratings assigned for these types of problems is determined by the relative expertise of the underwriter. Accordingly, management may optionally allow only expert underwriters to underwrite problems for which no information on corresponding impairments exists in underwriting knowledge base 24.

To briefly summarize, if an expert module does not exist for a particular problem, the system determines whether or not textual information regarding the corresponding impairment exists in underwriting knowledge base 24 (block 98). If not, the problem falls into the "relatively obscure" category and is underwritten (or referred to others for further consideration) without the benefit of underwriting knowledge base 24 (block 100). If the knowledge base does contain textual information dealing with the problem and its corresponding impairment, this textual information is displayed for use by the underwriter in determining the weights to be assigned to the problem (block 102). Although in many cases this approach to underwriting may be relatively straight forward, a greater degree of subjectivity is often involved.

UNDERWRITING USING INFORMATION DISPLAY

For medical problems which are to be underwritten by reference to textual information in underwriting data base 24 (i.e., information display), the underwriter is first offered the opportunity to review information about the basic body systems affected by the problem. This information is typically in the form of an introduction to the body systems, an outline (flow chart) of approaches to underwriting various impairments associated with the body systems, and medications used to treat various impairments of the subject body systems. For each problem/impairment identified, including non-medical/avocational and financial problems, the underwriter may review the textual information in underwriting data base 24 which relates to and describes the approach to underwriting the particular problem. This text is normally in the form of a general introduction to the impairment, a description of key data and strategies used for underwriting the subject problem, suggestions as to any additional information that should be obtained to adequately underwrite the case, and the specific underwriting action recommended, including any other additional factors which should be considered. The text normally identifies specific weights (i.e., debits or credits) which are to be assigned to the specific problem. In some cases, an extra premium (either temporary or permanent) may be suggested in lieu of, or in addition to, the suggested weights.

After reviewing the textual information displayed, including the weights identified for the problem and any extra premiums suggested, the underwriter is prompted to assign the weights and/or premiums to the problem in question. It should be noted that the underwriter also has the option of leaving underwriting of a particular problem "unresolved" if additional information, consultations, or referrals are deemed necessary, as well as the option of declining coverage on the basis of any given problem.

UNDERWRITING USING EXPERT MODULE

Expert modules are programmed for many of the impairments in the underwriting knowledge base. These modules incorporate the same data and underwriting strategies present in the textual information in underwriting knowledge base 24, as derived from the underwriting manuals and overall expertise of the system developers. In addition to these data and strategies, logic is developed to further prioritize the sequence of questions employed to resolve a particular problem. These programs are developed in such a way that they produce an underwriting decision (i.e., an assignment of debits/credits for the problem under consideration, plus any extra premiums which may be applicable) using the least amount of information possible. Furthermore, the data requested is sought from the information in application data base 20, preferably without requiring input from the underwriter, and secondly from the underwriter in an interactive mode. Other data bases or sources of information may also be consulted for the needed data. This means that different sequences of data requests might occur in connection with the same problem, depending upon the amount of data captured in the process of data collection, entry and screening. In summary, assuming that adequate and appropriate information has been collected and stored in the system, a rating or weight for each problem is determined and assigned by the expert module using information contained in application data base 20 and/or input from the underwriter in response to queries put forth by the expert module, in accordance with the underwriting philosophy programmed into the system. If adequate information is not available, appropriate requests are generated to obtain additional information. This approach results in efficient, high quality, uniform underwriting of like problems on a case-to-case basis.

UNDERWRITING WITHOUT THE UNDERWRITING KNOWLEDGE BASE

When no expert module and no information display module exists (i.e., the problem/impairment is not found in underwriting knowledge base 24), the problem will normally be left "unresolved" and the next problem will be taken up, unless the underwriter is rated as an "expert" in the subject area of concern Expert underwriters will be queried for the type of action to take (e.g., decline the case, leave the problem "unresolved", or take an underwriting action). The decision to take an underwriting action proceeds on the same basis as underwriting using the information display (i.e., weights are assigned, premiums (if appropriate) are accessed and the numbers of years they apply are specified, etc.).

After a particular problem has been underwritten in one of the three fashions described above, the system determines whether or not other problems in the subject application remain to be underwritten (block 104). If so, the remaining problems are taken in turn. If not, the system proceeds to an optional profiling process represented by block 106.

When no other problems remain to be underwritten, user adopted statistical profiles may be used to adjust one or more of the weights assigned to selected problems on the basis of previously stored statistical profiles relating to the selected problems. A profile is developed when a statistically proven correlation affecting the final rating or weight applicable to a particular problem has been found to exist, and the subject correlation is not reflected in the treatment of the impairment in underwriting data base 24. For example, a cardiovascular profile has been developed which adjusts the overall mortality risk on the basis of factors shown by studies to be predictive of premature mortality from arteriosclerotic heart disease (i.e., factors such as high cholesterol and high blood pressure). System switches are available which allow management, as a matter of policy, to either use or bypass profiles in the system. Additional profiles can be added as statistical correlations warrant.

After the individual weights are assigned to each problem, and after the weights are adjusted according to any applicable statistical profiles, the weights must be combined to determine an overall risk assessment for the case. There are several ways in which this can be done. For example, one method is to compare the individual weights to a standard mortality rating to determine a mortality ratio for each problem. The individual ratios can then be combined to determine an overall mortality ratio for the individual. In determining the final ratio, it has been found that certain problems or impairments interact to produce positive or negative effects that are not truly represented by a simple additive combination. Block 108 of FIG. 6 represents the process of combining the weights or ratios assigned to individual problems to determine a final ratio or rating. The process of block 108 includes the process of identifying combinations of problems which represent more or less severe impairments than would result if the subject problems occurred individually, and adding (or subtracting) an extra "combination" weight to the total. For example, if an applicant has hypertension (problem A) and is a diabetic (Problem B), individual weights or ratios would be assigned for problem A and problem B, in accordance with the methodology described above, and then the system at block 108 would assign an additional weight or ratio upon recognizing the existence of problems A and B in combination.

When the combined weight or mortality ratio has been determined, this figure is converted into a risk classification (block 110). This process permits the underwriter to correlate the expected mortality of the proposed insured (i.e., the mortality ratio), with actuarial analysis and pricing assumptions made during development of particular products (i.e., types of insurance plans). Proper assignment of risk classifications to each individual case insures the eventual billing of premiums in appropriate amounts to assure profitability at the levels expected from the actuarial pricing assumptions employed. This becomes increasingly important as expanding portfolios of products are underwritten, some of which may have relatively large differences in mortality assumptions built into the product designs.

A simplified example of a mortality plan conversion table (block 112) which may be used in converting the combined weight or mortality ratio to a risk classification appears as follows:

| MORTALITY PLAN CONVERSION TABLE Plan of Insurance Identifier X(8) | |
|---|---|
| Rating or Risk Classification | Mortality Ratio |
| Preferred Standard | 75% |
| Standard | 100% |
| Table A | 125% |
| Table B | 150% |
| " | 175% |
| " | 200% |
| " | 225% |
| " | 250% |
| " | 275% |
| Table H | 300% |

Use of such a table may be correlated with classes of mortality, such as aggregate mortality versus distinctive subgroup mortality (i.e., smokers, non-smokers, etc.), and with product benefits for the individual applicant. The mortality plan conversion table is preferably part of installation specific data base 22.

As noted above, there are other methods, in addition to the one just described, which may be used to determine the overall risk assessment. These include use of the excess death rate (EDR) or use of an exponential function.

After mortality plan conversion is complete, the system has determined a risk classification which is appropriate in view of the total mortality rating or ratio of the applicant and the particular plan of insurance selected.

The underwriter now exits the underwriting subroutine represented by block 62 of FIG. 4, and may elect to perform a business analysis subroutine represented by block 63.

Upon entry into the business analysis subroutine (FIG. 7), the system first determines whether or not the assigned underwriter is deemed to have sufficient expertise to override the rating or risk of classification just arrived at by the system (block 114). If yes, the underwriter is given an option to override the determined rating (block 116). If not, or if a qualified underwriter chooses not to override the rating, the system provides the underwriter an option to transfer the case for consultation to another underwriter or to a medical director (block 118). When the underwriter is not rated an expert underwriter but wants to override the system's rating, the application must be transferred to an expert rated underwriter (block 120). Once responsibility for the application has been transferred, the newly assigned expert underwriter may then override the system, if the situation warrants. When a decision is made to override the system, items such as amount of insurance, risk classification, extra premiums assessed, and number of years extra premiums apply may be modified. When a case is overridden, the reasons underlying the change must be documented when the change is made (block 122). After each proposed insured on a given application has been evaluated in this manner, a final underwriting action for the policy is determined.

If an expert underwriter decides to override the system determined rating, the option to determine the economic impact of a rating change is offered (block 124). If the underwriter decides to exercise this option, the system proceeds to a financial analysis generally represented by block 126 of FIG. 7. The system of the present invention preferably uses techniques of decision analysis to assess the economic impact on expected profitability of proposed changes in the possible courses of action for each individual application.

Decision analysis is a quantitative technique for making decisions about complex problems in situations of uncertainty. Use of decision analysis techniques normally involves five steps: (1) determining the possible options; (2) determining the probabilities of occurrence associated with each of the options; (3) quantifying the results of each of the options; (4) calculating the value of each of the options; and (5) determining the best option to select for a given situation and evaluating the effects of changes in the situation upon given options. In underwriting life insurance, the options available are normally those with which an underwriter deals on an every day basis, i.e., offer standard coverage, offer modified (substandard) coverage, or decline to offer coverage. The applicable probabilities are those relating to early mortality, given the existence of a particular problem, such as an abnormal test result secondary to any one of a number of underlying causes. The result of each option is the profit or loss which the insurance company will experience if that option is exercised. The "best" option is normally the one which will result in a maximization of profit.

A hypothetical example of the application of decision analysis in the system of the present invention involves a fifty-five-year-old applicant who is applying for $100,000 insurance coverage. The applicant is without physical complaints, but has an abnormality (a solitary pulmonary nodule) which was revealed on a routine chest x-ray. For clinical and insurability purposes, the disease with which one would be most concerned is lung cancer. There are no previous x-rays available for comparison. A pulmonary consultant has examined the applicant and recommended that surgery not be performed at this time, but that a repeat x-ray be taken in several months.

Figure 11:
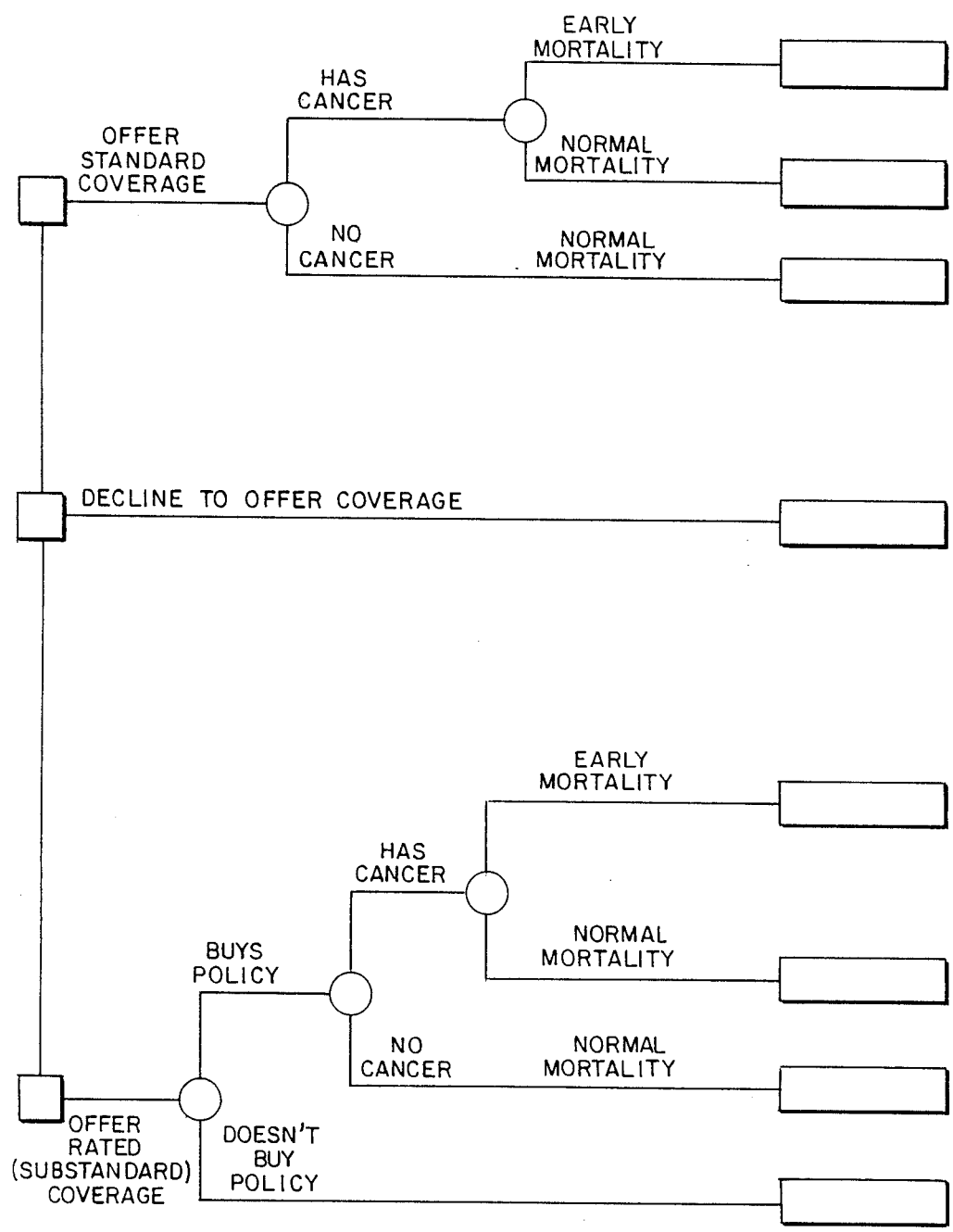
FIGS. 11-12 show decision trees which illustrate the use of decision analysis techniques in the system of the present invention.

The possible options available to the underwriter (i.e., offer standard coverage, decline coverage, offer rated or modified coverage), and the possible results flowing from each option, are illustrated in the decision tree of FIG. 11. To determine the probabilities of each result, the clinical and insurance literature must be consulted. At this point, the diagnosis is not clear. Although there is little information in the insurance literature regarding this impairment, there is a considerable amount of quantitative clinical information available on the problem of solitary pulmonary modules. In the clinical literature, a quantitative system by which the probability of malignancy can be estimated utilizing Bayes Theorem of Probabilities has been developed. Using this system, the probability of the existence of cancer in this particular case is determined to be 86% (0.86).

To complete the analysis, additional probabilities must be supplied or estimated. For example, the best possible two-year survival rate for lung cancer is 46% (0.46). Since the applicant is currently asymptomatic and not under treatment of a doctor, the probability of acceptance of a rated policy is estimated to be 50% (0.50). These probabilities (P) and the associated alternative probabilities (1-P) are identified with the appropriate branches of the decision tree, as shown in FIG. 12.

The results of each outcome, in terms of profit or loss to the company, may be quantified as follows:

1. A profit of $490 will be realized if a $100,000 standard policy is offered and accepted and mortality is normal;
2. A loss of $100,000 will result if a policy is offered and accepted, and there is early mortality;
3. A loss of $10.00 (for processing) will result if coverage is declined (i.e., a policy is offered and declined, or not offered); and
4. A profit of $889.00 will result if a rated policy is offered and accepted, and mortality is normal.

Figure 12:
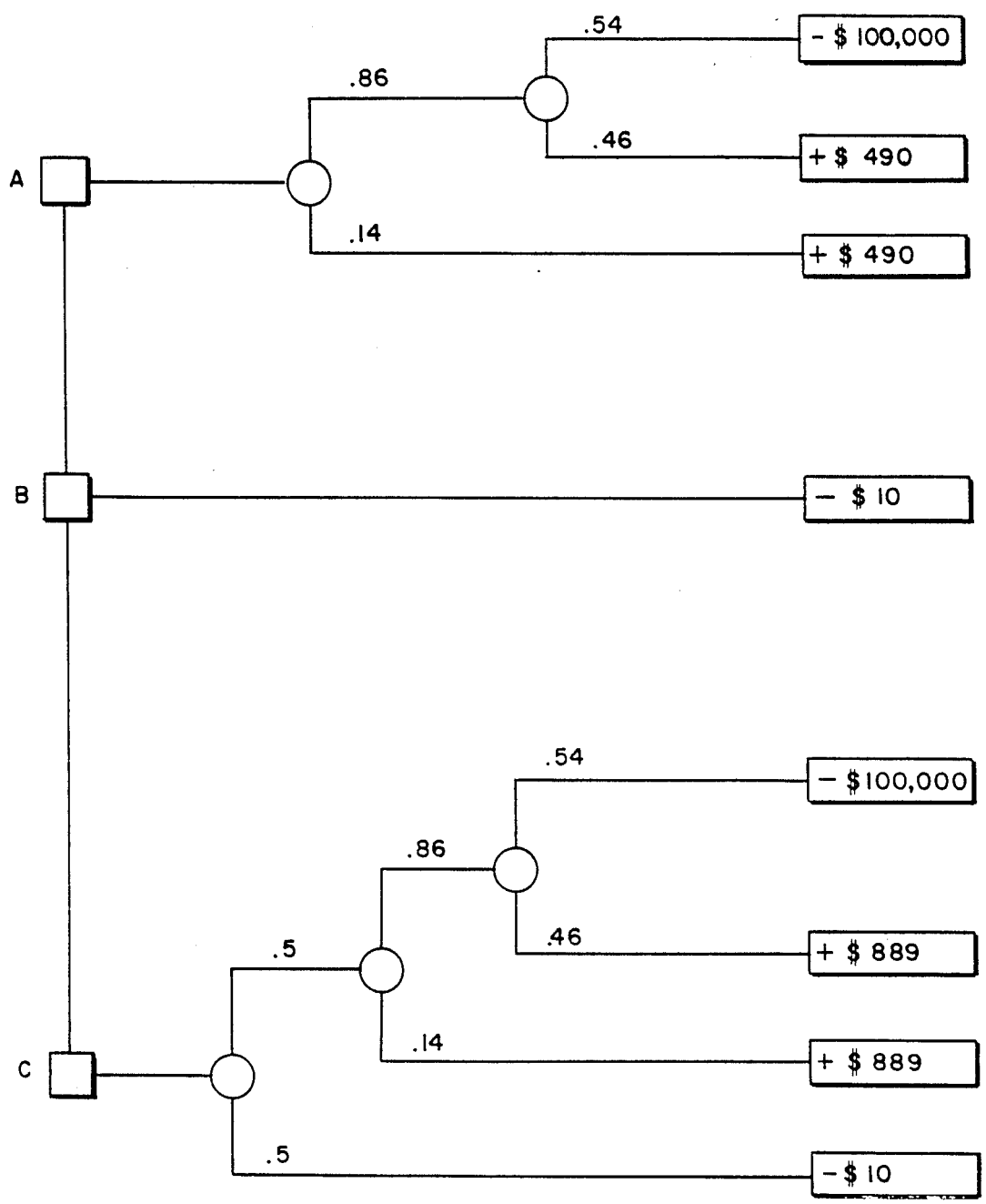

FIG. 12 shows the decision tree of FIG. 11 with the probabilities and profit and loss figures shown on the appropriate branches. The values of each option, in terms of profit or loss to the company, can then be determined by the following calculations:

$$
\begin{aligned}
A &= .14(\$490) + .86[.46(\$490) + .54(-\$100,000)] \\
  &= -46,177 \\
B &= 1.0(-\$10) \\
  &= -10 \\
C &= .5(-\$10) + .5[.14(\$889) + .86[.46(\$889) + .54 \\
  &\quad (-\$100,000)]] \\
  &= -22,986
\end{aligned}
$$

From these calculations, it is apparent that the appropriate option to select is option B (i.e., decline to offer coverage).

Use of this technique to evaluate "close" cases or to allow the underwriter to assess the impact of a contemplated rating change, will allow the individual underwriter and the company (through appropriate entries made in the management information data base) to determine the impact of such cases and changes on the company's profitability. These techniques can also lead to more uniform and rational decision making by individual underwriters and groups of underwriters.

After exiting the business analysis subroutine (block 63 of FIG. 4), the program records appropriate information relating to the subject application and underwriter in the management information data base (block 86) making the information available for subsequent administrative processing. The system then offers the underwriter the option to select and underwrite another case or to exit the system (block 88).

From the preceding description of the preferred embodiment, it is evident that the objects of the invention are attained. As previously noted, the invention has been described and illustrated in detail by reference to a particularly preferred embodiment adapted for use in the field of life insurance. Although the present invention does offer particular advantages in this field, it is felt that adaptation and application of the method and apparatus of the present invention to other fields will also be advantageous. Accordingly, the spirit and scope of this invention are not to be limited by the details of the preferred embodiment described above, but rather by the terms of the appended claims.

BLOOD PRESSURE HYPERTENSION
(Elevated Blood Pressure)

INTRODUCTION

BLOOD PRESSURE

Blood pressure is the force exerted on the arterial walls by the flow of blood from the heart. It is determined by the cardiac output (heart rate per minute times the volume of blood ejected by the left ventricle per beat) and the peripheral vascular resistance (the resistance to blood flow offered by the peripheral blood vessels.) Blood pressure is not static; rather, it fluctuates during the day in response to changes in physical activity, emotional stress, and other factors.

Blood pressure, like atmospheric pressure, is measured in terms of millimeters of mercury (mm Hg). Two readings are of importance: the pressure occurring when the heart contracts (systolic) and when the heart is at rest (diastolic). Blood pressure readings are expressed as a relationship between systolic and diastolic blood pressure as follows:

140/80 means that Systolic Blood Pressure is 140 mm Hg, and Diastolic Blood Pressure is 80 mm Hg.

HYPERTENSION

Hypertension ("high blood pressure") is a sustained elevation of blood pressure above the range considered normal for a given age and gender. If left untreated, individuals with hypertension will generally experience significantly greater mortality than those who have normal blood pressure.

Hypertension damages the heart by causing it to work harder to pump blood throughout the body. The increased strain forces the heart muscle (particularly the left ventricle) to enlarge. If the underlying cause of the high blood pressure is not treated, the heart may be unable to compensate sufficiently and congestive heart failure may result.

Other organs of the body are also adversely affected by hypertension. The kidneys may respond to hypertension by becoming irreversibly scarred (nephrosclerosis). Serum proteins and blood can then leak into the urine, and chronic renal failure may ensue. In the brain, the blood vessels may become prematurely atherosclerotic and/or fragile, and strokes or transcient ischemic attacks (TIAs) may occur.

Hypertension is a significant risk factor for the development of arteriosclerosis. When hypertension is combined with a history of smoking, high serum cholesterol, obesity, and/or a family history of cardiovascular disease, the patient is at particular risk for the development of a myocardial infarction, stroke, and peripheral vascular disease.

Primary or essential hypertension is diagnosed when the fundamental cause of the elevated blood pressure is unknown. Factors associated with the development of essential hypertension include: positive family

HYPERTENSION — cont'd history of hypertensive disease, high salt intake, obesity, certain types of psychological stress, smoking, and a heavy intake of alcohol.

The term secondary hypertension refers to hypertension that has a known cause. This type of hypertension can often be cured through successful treatment of the underlying disorder. Impairments such as renovascular stenosis (narrowing of one or more of the large renal arteries), endocrine tumors (pheochromocytoma), coarctation of the aorta, and the administration of oral contraceptives are causes of secondary hypertension.

Mild and moderately elevated blood pressure may produce no symptoms or be associated with dizziness, palpitations, or easy fatigability. Severely hypertensive patients may experience headaches, nosebleeds, hematuria, and blurred vision.

The evaluation of hypertension begins with information about the relevant medical history and a current physical examination. The blood pressure is measured and the retina is closely examined. Any damage to the small vessels in the retina can be readily observed (see *Hypertensive retinopathy* in the *COMPLICATIONS* section below), and assist in the determination of the severity of disease. Because the heart can be damaged by hypertension, an ECG is commonly obtained in order to determine if there is evidence of left ventricular hypertrophy.

TREATMENT

Once hypertension is diagnosed, treatment is started to reduce the blood pressure to the normal range. It is important to determine if the applicant has complied with treatment and maintained a fairly consistent blood pressure; hypertensive individuals whose blood pressure has been successfully controlled at normal levels for a period of time may experience little or no excess mortality.

Treatment of mild essential hypertension usually begins with an alteration of diet and lifestyle. Weight loss, reduction of harmful stress, increased exercise, and a restriction in the intake of salt, coffee, and alcohol are recommended. Other risk factors which contribute to the development of coronary artery disease, such as cigarette smoking and elevated cholesterol, are eliminated if possible.

If the blood pressure continues to be elevated, drug therapy is begun. There are generally four classes of drugs used in the treatment of hypertension. In most cases, the mechanism of action of these medications is related to their ability to decrease either the cardiac output and/or the peripheral vascular resistance. (See *MEDICATIONS* in the INTRODUCTION to the CIRCULATORY SECTION.)

- Diuretics decrease blood pressure by enhancing the elimination of sodium and water from the body and by decreasing peripheral vascular resistance.
- Antiadrenergic agents act on the center in the brain which controls blood pressure, on the nerves that cause the release of hormones (adrenalin, etc.) that modulate blood pressure, or by blocking the sites on the tissues where these hormones act (blood vessels, heart, adrenal glands, etc.).
- Vasodilators decrease peripheral vascular resistance by dilating the arteries via a direct relaxation of the muscle cells in the artery walls.
- Angiotensin blockers reduce blood pressure by inhibiting the production and/or action of angiotensin. Angiotensin is a hormone which increases peripheral vascular resistance by causing the blood vessels to constrict.

Each drug used has different degrees of potency and some are associated with undesirable side effects such as dizziness, fatigue, and nausea. Treatment is tailored to the patient; in general the significance of the disease increases with the number of drugs prescribed.

COMPLICATIONS

Complications, sometimes referred to as target organ or end organ damage, are the consequence of chronic hypertension; examples include hypertensive encephalopathy, hypertensive retinopathy, heart enlargement or ECG abnormalities, and nephrosclerosis.

The retina is the only tissue in which the arteries can be examined directly to observe the progress of the vascular effects of hypertension. Hypertensive retinopathy refers to damage of the retina due to elevated blood pressure. Increasing severity of hypertension is associated with focal spasm, progressive narrowing of the arterioles, leakage of blood or plasma from these vessels (exudates), and edema of the optic nerve (papilledema). Hypertensive retinopathy can be classified into grades, reflecting the severity of the disease:

CLASSIFICATION OF HYPERTENSIVE RETINOPATHY

| Degree | General Narrowing AV ratio* | Focal spasm** | Hemorrhages | Exudates | Papilledema |
|---|---|---|---|---|---|
| Normal | 3:4 | 1:1 | No | No | No |
| Grade I | 1:2 | 1:1 | No | No | No |
| Grade II | 1:3 | 2:3 | No | No | No |
| Grade III | 1:4 | 1:3 | Yes | Yes | No |
| Grade IV | Fine, fibrous cords | Obliteration of distal flow | Yes | Yes | Yes |

*The ratio of arteriolar to venous diameters.
**The ratio of diameters of region of spasm to proximal arteriole.

Heart enlargement, usually left ventricular hypertrophy (increased muscle mass of the left ventricle) and ECG abnormalities are caused by the extra work the heart must perform in order to pump blood in the hypertensive patient. Heart enlargement may be discovered with a chest X-ray, from chest palpation during a physical exam, from some special study such as an echocardiogram, or with an ECG. The generally accepted ECG criteria for the diagnosis of left ventricular hypertrophy consists of an R wave in lead $V_5$ and an S wave in lead $V_1$ that total 35 mm or more in deflection plus a left ventricular "strain" pattern (ST segment depression and T wave inversion).

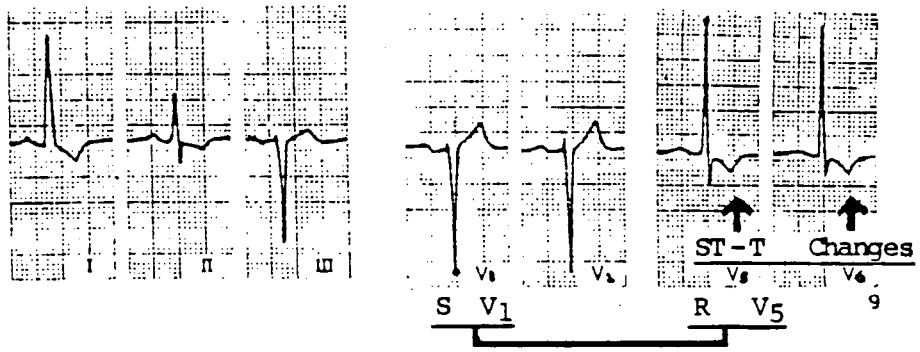

Hypertensive encephalopathy is a syndrome in which severe hypertension is associated with symptoms of nervous system dysfunction such as confusion, blurred vision, somnolence, headache, and nausea. Severe cases may progress to seizures, coma, and eventually death. If the hypertension is controlled before permanent brain damage occurs, a full recovery without residual effects is possible.

Hypertensive nephrosclerosis refers to disease of the small kidney arteries due to hypertension. Some cases may be gradual and consist only of an accelerated arteriosclerosis of the renal arteries. More severe cases involve actual necrosis (cell death) of the renal arteries, and progressive deterioration and renal failure may result. Hematuria, marked proteinuria, and an elevated BUN and creatinine are usually seen with more severe involvement. These abnormalities may diasappear if the hypertension can be successfully controlled.

COMPLICATIONS — cont'd

Other names for severe elevated blood pressure that result in target organ damage are accelerated and malignant hypertension. Accelerated hypertension describes a significant recent increase in blood pressure levels with associated retinal hemorrhages and/or exudates, but no papilledema. Malignant hypertension refers to marked hypertension associated with papilledema. In both of these conditions, blood pressures are dangerously elevated (usually 180/130 or higher) and there may be symptoms such as headache, blurred vision, advanced retinopathy, heart enlargement, congestive heart failure, and renal failure. Malignant hypertension calls for emergency treatment to lower blood pressure and prevent further complications. Even though the blood pressure may be maintained at greatly reduced levels, the damage done during the hypertensive crisis is often permanent and may require an extra rating.

UNDERWRITING CONSIDERATIONS

Through the years, many types of averaging systems have been utilized to determine a representative blood pressure reading to be used to enter a table for rating purposes. In the past, much weight was placed on the historical readings, and a person was sometimes "penalized" for being on treatment. Currently, medical opinion favors reducing blood pressure levels to a normal range as quickly as possible.

The basic system employed in the guide for determining the Table Entry Blood Pressure is a one-year average. This One-Year Table Entry Average is the average of all one-day pressures within one year of the application, including those on the current insurance examination. A one-day pressure is the average of all pressures taken on the same day. The resulting one-year average blood pressure should be used in the table to determine the debits.

Since no averaging rule is universally satisfactory, adoption of the One-Year Table Entry Average, aside from its simplicity, has the advantage of favoring those whose pressures have responded to medical therapy. Considerable judgment is necessary to be certain the Table Entry Average is truly representative of the individual's risk. Consider the following examples. An individual with several readings taken within the year, all of which are fairly consistent and similar to the blood pressure on exam, will have a table entry average that is likely to be representative of that person's true blood pressure. However, another individual, with several high pressure readings prior to one year ago, but with none taken within the year, doesn't "fit" the one-year average guideline. A single blood pressure reading on exam may not be representative of that person's true pressure. The underwriter should request several additional readings to be taken on different days to determine a representative table entry pressure.

Hypertensive applicants generally tend to fall into one of three categories based on blood pressure trends (see illustration). Because more people are receiving effective antihypertensive therapy, we are seeing an increasing incidence of those with improving pressures. Individuals whose pressures are continuing to increase should be underwritten with extreme caution, as should other individuals whose pressures do not respond well to treatment.

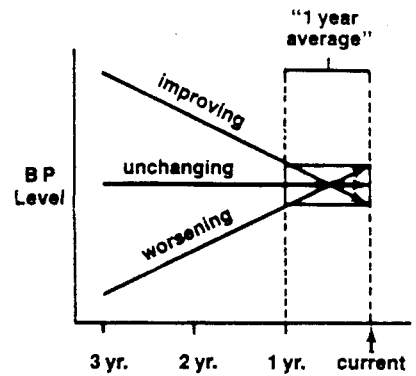

Debits in the BASIC TABLE reflect: (a) results of the 1979 intercompany Blood Pressure Study; and (b) anticipation of further mortality improvements. These improvements are expected as a result of ever-increasing public awareness of the significance of hypertension, earlier detection and treatment, and better long-term adherence to therapeutic management.

One reason to apply basic debits for uncomplicated hypertension is to account for the probability of eventually developing complications. When complications ALREADY exist, this signifies high-risk stages of disease for which basic table debits are inadequate. If pressures are satisfactorily controlled with antihypertensive drugs, further development of complications may be slowed or even stopped. Prognosis is especially poor, however, if pressures remain high.

UNDERWRITING CONSIDERATIONS — cont'd

UNDERWRITING FOCUS

History? Must be aware of elevated blood pressures in the past even if current pressures are normal. A downward trend is favorable.

How long have pressures been elevated? High pressure sustained over many years is worse than such pressure of short duration.

Current BP levels? Elevated pressures on current examination — without a history of hypertension — can indicate an uncertain future.

Has the proposed insured adhered to an effective therapeutic program? Documentation of steadily improving pressures would suggest an effective program.

Type and amount of medication? Blood pressures lowered to normal levels with treatment are considered favorable, but the number of medications and/or the amount can indicate the severity. Current elevated pressures suggest poor medical management.

Complications? "Target organ" damage can indicate chronic hypertension.

Other impairments? Elevated blood pressure combined with certain impairments such as coronary heart disease, cerebrovascular disease, diabetes, and chronic obstructive lung disease, create a combined risk greater than the sum of the two. Additional debits are required.

Secondary hypertension? An additional rating may be necessary for cause.

Accelerated/malignant hypertension? If suspected currently or not controlled, a declination is required.

WORKUP

*APS(s) with inquiry about past blood pressure readings and any treatment; EXAM; HO Micro; if warranted, an additional blood pressure reading on a separate day; for large amounts, ECG*

BLOOD PRESSURE*

UNDERWRITING ACTION

Secondary hypertension (hypertension known to be caused by another impairment)

1. Determine rating for cause of hypertension
2. Add rating for hypertension itself following steps for *Primary* below

Primary hypertension

1. Use One-Year Average and enter table to determine basic blood pressure debits

MALES

SYSTOLIC

| DIASTOLIC | Age | To 140 | 141-150 | 151-160 | 161-170 | 171-180 | 181-190 | 191-200 | 201-210 |
|---|---|---|---|---|---|---|---|---|---|
| To 80 | 15-34 | 0 | 0 | 20 | 45 | 75 | 105 | 140 | 175 |
|  | 35-44 | 0 | 0 | 10 | 35 | 65 | 90 | 125 | 160 |
|  | 45-54 | 0 | 0 | 5 | 25 | 55 | 80 | 115 | 150 |
|  | 55 up | 0 | 0 | 0 | 20 | 45 | 70 | 105 | 140 |
| 81-85 | 15-34 | 0 | 10 | 35 | 55 | 85 | 120 | 155 | 190 |
|  | 35-44 | 0 | 0 | 25 | 45 | 70 | 100 | 135 | 170 |
|  | 45-54 | 0 | 0 | 15 | 35 | 60 | 90 | 125 | 160 |
|  | 55 up | 0 | 0 | 10 | 30 | 50 | 80 | 115 | 150 |
| 86-90 | 15-34 | 5 | 25 | 55 | 80 | 105 | 140 | 180 | 225 |
|  | 35-44 | 0 | 10 | 40 | 65 | 90 | 120 | 160 | 200 |
|  | 45-54 | 0 | 5 | 25 | 50 | 75 | 105 | 145 | 185 |
|  | 55 up | 0 | 0 | 15 | 40 | 65 | 95 | 135 | 175 |
| 91-95 | 15-34 | 30 | 50 | 75 | 105 | 135 | 170 | 210 | 255 |
|  | 35-44 | 15 | 35 | 60 | 90 | 120 | 155 | 195 | 240 |
|  | 45-54 | 5 | 25 | 45 | 75 | 105 | 140 | 180 | 225 |
|  | 55 up | 0 | 15 | 35 | 65 | 95 | 130 | 170 | 215 |
| 96-100 | 15-34 | 55 | 75 | 105 | 140 | 175 | 215 | 260 | 310 |
|  | 35-44 | 35 | 55 | 85 | 120 | 155 | 195 | 240 | 290 |
|  | 45-54 | 20 | 40 | 70 | 105 | 140 | 180 | 225 | 275 |
|  | 55 up | 10 | 30 | 60 | 95 | 130 | 170 | 215 | 265 |
| 101-105 | 15-34 | 90 | 115 | 150 | 185 | 225 | 270 | 320 | 370 |
|  | 35-44 | 65 | 90 | 125 | 160 | 200 | 245 | 295 | 345 |
|  | 45-54 | 45 | 70 | 105 | 140 | 180 | 225 | 275 | 325 |
|  | 55 up | 30 | 55 | 90 | 125 | 165 | 210 | 260 | 310 |
| 106-110 | 15-34 | 140 | 170 | 205 | 240 | 280 | 325 | 380 | 430 |
|  | 35-44 | 110 | 140 | 175 | 210 | 250 | 295 | 350 | 400 |
|  | 45-54 | 80 | 110 | 145 | 180 | 220 | 265 | 320 | 370 |
|  | 55 up | 60 | 90 | 130 | 165 | 205 | 250 | 305 | 355 |
| 111-115 | 15-34 | 205 | 235 | 270 | 305 | 345 | 390 | 440 | 480 |
|  | 35-44 | 170 | 200 | 235 | 270 | 310 | 355 | 405 | 445 |
|  | 45-54 | 140 | 170 | 205 | 240 | 280 | 325 | 375 | 415 |
|  | 55 up | 120 | 150 | 185 | 220 | 260 | 305 | 355 | 395 |

*Outside printed range .................................................................... see MD 2. Female Adjustment ....................................... reduce table debits by 20%

ADDITIONAL CONSIDERATIONS that modify the ratings above

Blood pressure trends — If a progressive worsening in
blood pressure has occurred in the previous months .................... increase rating by 50 up

Complications

Malignant or accelerated hypertension, hypertensive
crisis, and hypertensive encephalopathy
Current ............................................................................................ Dec
Recovered, with good control of blood pressure
0-1 yr since recovery ...................................................................... PP
1-3 ...................................... see MD — for best cases, add 100 to blood pressure rating 3 up ...................................... rate on the basis of the *One-Year Table Entry Average*

ADDITIONAL CONSIDERATIONS — cont'd

Retinopathy (see above for Grade)
        Grade I, II, or described as "mild" .................................................. add 0

III ............................... see MD — for best cases, add 100 to blood pressure rating IV .................................................................... Dec Heart enlargement ...................................... see HEART ENLARGEMENT ECG abnormalities .......................... sum debits — apply the highest suggested ECG rating if a range is given Proteinuria ............................................................ see PROTEINURIA

Combinations

Coronary heart disease .............................. see CORONARY HEART DISEASE Diabetes ................................................. see DIABETES MELLITUS Cerebrovascular disease ........................... see CEREBROVASCULAR DISEASE COPD ............................................... see CHRONIC OBSTRUCTIVE PULMONARY DISEASE

Credits\* — Normal resting ECG within 1 year, or normal treadmill ECG within 2 years

| Pressure Debits | Age to 44 | | Age 45 up | |
| --- | --- | --- | --- | --- |
| | Resting ECG | Treadmill ECG | Resting ECG | Treadmill ECG |
| to 150 | 15 | refer to EXERCISE ECG | 25 | refer to EXERCISE ECG |
| 151 up | 15 | | 25 | |

\*Do not apply when there are Complications or Combinations.

PRO•file Analysis
    Credits or debits should be used

SPECIAL NOTE: When a Table Entry blood pressure requires a rating, the PRO•file BP score should be "0" instead of " − 2"

Cigarette smoking
        Current or within one year
            Up to two packs per day ................................................. add 0
            More than two packs per day ............................................ add 50

Over one year ago ......................................................... add 0

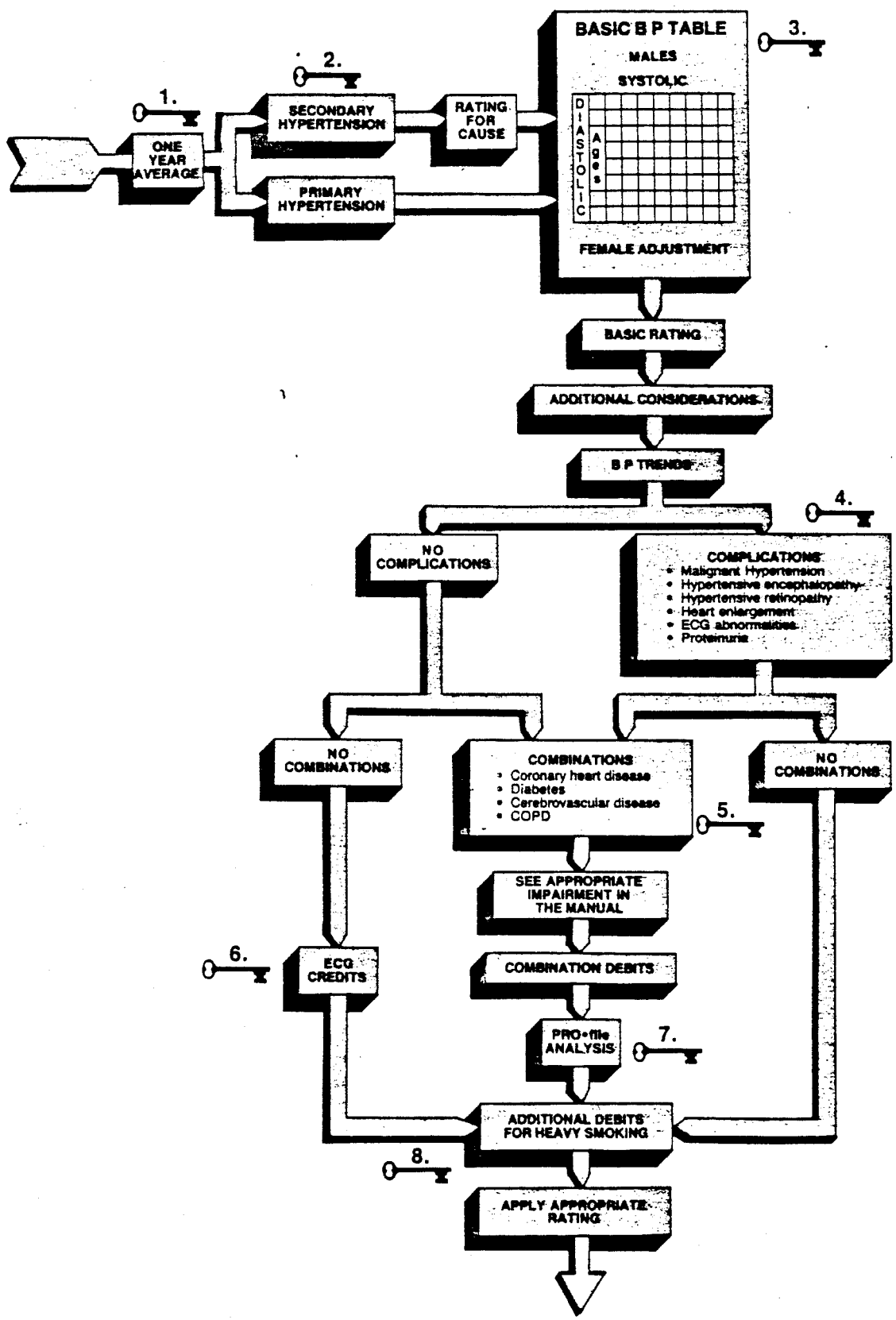

APPRAISAL OF ELEVATED BLOOD PRESSURE
(considerations; comments)

1.

ONE-YEAR TABLE ENTRY AVERAGE is the average of all one-day pressures within one year of the application, including those on the current insurance examination. A one-day pressure is the average of all pressures taken on one day. A pressure so out of line (high or low) as to suggest a false representation should be discarded.

2.

SECONDARY HYPERTENSION can be caused by kidney disease, tumors or hyperplasia of the adrenal glands, hyperthyroidism, or coarctation of the aorta. If a cause is identified and successfully treated, pressures often return to normal. Unlike primary (essential) hypertension, where no cause is known, debits for secondary hypertension have to be increased by the debits required for its cause.

3.

BASIC TABLE. Broad ranges for systolic and diastolic pressures are used in this table to create large differentials between adjacent debits. Underwriters then have the opportunity to choose higher or lower debits based on (a) arithmetic considerations — closeness of the one-year average to adjacent "debit blocks"; and (b) judgmental considerations that distinguish better from worse risks.

ADDITIONAL CONSIDERATIONS

4.

COMPLICATIONS of severe, chronic hypertensive disease can include damage to the cardiovascular system (often called "target organ damage"). Examples are (a) hypertensive encephalopathy, (b) hypertensive retinopathy, (c) heart enlargement, (d) ECG abnormalities, and (e) kidney damage, as evidenced by proteinuria. Other significant disorders that complicate the appraisal of elevated blood pressure include accelerated and malignant hypertension, both of which, unless brought under control, indicate a poor prognosis.

5.

COMBINATIONS. Certain impairments, combined with hypertension, create a composite risk that exceeds the sum of the debits for the two. These combination impairments such as coronary heart disease, diabetes, cerebrovascular disease, and chronic obstructive pulmonary disease may require additional debits or declination.

6.

ECG CREDITS for normal resting ECG within one year, or normal treadmill ECG within two years are subtracted from the basic table rating unless there are complications or combinations.

7.

PRO•file ANALYSIS debits or credits should be applied where applicable.

8.

HEAVY CIGARETTE SMOKING (two or more packs per day) should be assessed an additional 50 debits in addition to the basic PRO•file debits or credits above.

BUILD
Weight Abnormal

The relationship between overweight and mortality has been the subject of controversy in recent years in spite of the consistent finding of increased mortality among insured lives who were overweight at the time of underwriting. The *1979 Build Study* focused on the mortality influence of relative weight (i.e., ratio of actual weight to corresponding sex/height-distinct average weight). Many population studies, however, focus on other measures of weight (e.g., body mass index; ponderal index; Sheldon index; Broca), producing findings that are difficult to use or interpret. Because of these difficulties and because height and weight measurements are still encountered most frequently, this manual will continue to use relative weight to determine abnormal build ratings.

BUILD CHART

Build charts are available for adult males and females (ages 15 up) and for juveniles. Height is given in feet and inches, and weight in pounds. Conversion factors are listed in a table below the build charts to aid translations from metric measurements. Interpolation between debit categories may be required to arrive at an appropriate number of debits. When using height categories, fractions of less than one-half inch should be dropped, and fractions one-half inch or larger should be raised to the next higher inch.

Marked overweight or underweight should be evaluated carefully. Significant overweight is commonly associated with cardiovascular problems. Marked underweight can indicate a person in poor general health, which may be the result of cancer, cardiovascular diseases, alcohol or drug abuse, chronic obstructive pulmonary disease, or significant infectious diseases.

WEIGHT CHANGE

A sudden, recent unexplained weight change (over 15 pounds for males and over 10 pounds for females) must be evaluated for a possible related serious illness. Recent unexplained weight loss can result from serious diseases such as those mentioned above, as well as Acquired Immune Deficiency Syndrome (AIDS), and digestive disorders. These situations require underwriting caution — postponement may be the best action.

In the case of recent (within the year) voluntary dietary weight loss, the current weight may be only a temporary condition. Weight gain to the former level or higher is possible. The underwriter should consider adding half the weight loss to the current weight to enter the BUILD CHART.

Surgery to achieve weight reduction should be classified under the type of surgery performed. Refer to DIGESTIVE SECTION, GASTROINTESTINAL SURGERY FOR OBESITY.

COMBINATION IMPAIRMENTS

The combination of overweight with some other impairments such as hypertension usually requires that the debits be summed. With other impairments, an abnormal build may add substantially to the mortality risk (e.g., overweight with coronary heart disease; underweight with chronic obstructive pulmonary disease; etc.). Debits in addition to the sum of the ratings are required. Guidance for these combination debit situations will be located in the *ADDITIONAL CONSIDERATIONS* section of the appropriate impairment.

UNDERWRITING FOCUS

Abnormal build? Use current (within 3 months) height and weight to determine debits from the BUILD CHART.
Weight change? Recent unexplained weight loss may be the result of an underlying condition.
Surgery performed to achieve weight loss? Surgery may be performed to prevent additional damage to the body from diseases that result from severe obesity. Refer to DIGESTIVE SECTION, GASTROINTESTINAL SURGERY FOR OBESITY.
Other complications/conditions? Other conditions in conjunction with an abnormal build can significantly increase the mortality risk.

WORKUP

*APSs; Exam and HO Micro if over 50 debits for abnormal build are required or if there are other complications*

UNDERWRITING ACTION

1. Determine the debits for abnormal build from the BUILD CHART.
2. If surgery has been performed to reduce weight, refer to DIGESTIVE SECTION, GASTROINTESTINAL SURGERY FOR OBESITY.
3. If other complications or conditions are present, refer to the appropriate impairment for additional instructions.

BUILD CHART
MALES and FEMALES
Ages 15 and over

| HEIGHT Ft. in. | UNDERWEIGHT DEBITS 25 | AVERAGE WEIGHT | OVERWEIGHT DEBITS | | | | | | | |
|---|---|---|---|---|---|---|---|---|---|---|
| | | | 25 | 50 | 75 | 100 | 125 | 150 | 200 | 250 |
| 4-10 | 78 | 120 | 156 | 173 | 187 | 198 | 206 | 214 | 222 | 227 |
| 11 | 81 | 124 | 161 | 179 | 193 | 205 | 213 | 221 | 229 | 236 |
| 5- 0 | 84 | 129 | 168 | 186 | 201 | 213 | 222 | 230 | 239 | 245 |
| 1 | 86 | 133 | 173 | 192 | 207 | 219 | 229 | 237 | 246 | 253 |
| 2 | 90 | 138 | 179 | 199 | 215 | 228 | 237 | 246 | 255 | 262 |
| 3 | 93 | 143 | 186 | 206 | 223 | 236 | 246 | 254 | 264 | 272 |
| 4 | 96 | 147 | 191 | 212 | 229 | 242 | 253 | 262 | 272 | 279 |
| 5 | 98 | 151 | 196 | 217 | 236 | 249 | 260 | 269 | 279 | 287 |
| 6 | 101 | 156 | 203 | 225 | 243 | 257 | 268 | 278 | 288 | 296 |
| 7 | 104 | 160 | 208 | 230 | 250 | 264 | 275 | 285 | 296 | 304 |
| 8 | 107 | 165 | 214 | 238 | 257 | 272 | 284 | 294 | 305 | 314 |
| 9 | 110 | 170 | 221 | 245 | 265 | 280 | 292 | 303 | 314 | 323 |
| 10 | 113 | 174 | 226 | 251 | 271 | 287 | 299 | 310 | 322 | 331 |
| 11 | 116 | 179 | 233 | 258 | 279 | 295 | 308 | 319 | 331 | 340 |
| 6- 0 | 120 | 184 | 239 | 265 | 287 | 304 | 316 | 328 | 339 | 348 |
| 1 | 124 | 190 | 247 | 274 | 295 | 312 | 325 | 336 | 348 | 357 |
| 2 | 127 | 195 | 254 | 281 | 302 | 320 | 333 | 345 | 357 | 365 |
| 3 | 131 | 201 | 261 | 289 | 312 | 328 | 342 | 354 | 366 | 374 |
| 4 | 134 | 206 | 268 | 297 | 317 | 336 | 350 | 363 | 375 | 381 |
| 5 | 137 | 211 | 274 | 304 | 325 | 342 | 357 | 369 | 382 | 388 |
| 6 | 141 | 217 | 282 | 312 | 334 | 352 | 367 | 380 | 391 | 397 |
| 7 | 145 | 223 | 290 | 321 | 341 | 359 | 375 | 388 | 399 | 406 |
| 8 | 148 | 228 | 296 | 328 | 349 | 367 | 383 | 394 | 406 | 413 |
| 9 | 152 | 234 | 304 | 337 | 358 | 374 | 391 | 402 | 414 | 421 |

JUVENILE BUILD CHART*

| AGES 0-2 | | | AGES 3-9 | | | AGES 10-14 | | |
|---|---|---|---|---|---|---|---|---|
| HT. | MIN. | MAX. | HT. | MIN. | MAX. | HT. | MIN. | MAX. |
| 24" | 8 | 23 | 30" | 18 | 40 | 48" | 44 | 92 |
| 26" | 10 | 26 | 34" | 22 | 44 | 52" | 54 | 108 |
| 28" | 13 | 31 | 38" | 26 | 54 | 56" | 63 | 126 |
| 30" | 15 | 36 | 42" | 32 | 64 | 60" | 74 | 144 |
| 32" | 18 | 40 | 46" | 38 | 78 | 64" | 87 | 166 |
| 34" | 21 | 42 | 50" | 46 | 94 | 68" | 100 | 186 |
| 36" | 23 | 45 | 54" | 56 | 111 | 72" | 113 | 206 |
| 38" | 26 | 48 | 58" | 66 | 128 | 76" | 126 | 228 |
| 40" | 29 | 52 | | | | | | |

*Outside printed range—individual consideration.

CONVERSION TABLES

WEIGHT — KILOGRAMS TO POUNDS  1 KG = 2.2046 lbs.

| KGS. | 40 | 50 | 60 | 70 | 80 | 90 | 100 | 110 | 120 | 130 |
|---|---|---|---|---|---|---|---|---|---|---|
| 0 | 88 | 110 | 132 | 154 | 176 | 198 | 220 | 243 | 265 | 287 |
| 1 | 90 | 112 | 134 | 157 | 179 | 201 | 223 | 245 | 267 | 289 |
| 2 | 93 | 115 | 137 | 159 | 181 | 203 | 225 | 247 | 269 | 291 |
| 3 | 95 | 117 | 139 | 161 | 183 | 205 | 227 | 249 | 271 | 293 |
| 4 | 97 | 119 | 141 | 163 | 185 | 207 | 229 | 251 | 273 | 295 |
| 5 | 99 | 121 | 143 | 165 | 187 | 209 | 231 | 254 | 276 | 298 |
| 6 | 101 | 123 | 146 | 168 | 190 | 212 | 234 | 256 | 278 | 300 |
| 7 | 104 | 126 | 148 | 170 | 192 | 214 | 236 | 258 | 280 | 302 |
| 8 | 106 | 128 | 150 | 172 | 194 | 216 | 238 | 260 | 282 | 304 |
| 9 | 108 | 130 | 152 | 174 | 196 | 218 | 240 | 262 | 284 | 306 |

HEIGHT — METERS TO FEET AND INCHES  1 M. = 39.37 In. (3.28 ft.)

| METERS | FT. | IN. | METERS | FT. | IN. | METERS | FT. | IN. |
|---|---|---|---|---|---|---|---|---|
| 1.47-1.48 | 4 | 10 | 1.67-1.68 | 5 | 6 | 1.87-1.89 | 6 | 2 |
| 1.49-1.51 | 4 | 11 | 1.69-1.71 | 5 | 7 | 1.90-1.91 | 6 | 3 |
| 1.52-1.53 | 5 | 0 | 1.72-1.73 | 5 | 8 | 1.92-1.94 | 6 | 4 |
| 1.54-1.56 | 5 | 1 | 1.74-1.76 | 5 | 9 | 1.95-1.96 | 6 | 5 |
| 1.57-1.58 | 5 | 2 | 1.77-1.79 | 5 | 10 | 1.97-1.99 | 6 | 6 |
| 1.59-1.61 | 5 | 3 | 1.80-1.81 | 5 | 11 | 2.00-2.01 | 6 | 7 |
| 1.62-1.63 | 5 | 4 | 1.82-1.84 | 6 | 0 | 2.02-2.04 | 6 | 8 |
| 1.64-1.66 | 5 | 5 | 1.85-1.86 | 6 | 1 | 2.05-2.07 | 6 | 9 |

What is claimed is:

1. Information processing apparatus for evaluating the insurability of a potentially insurable risk, comprising:
   a. means providing first and second data bases, an input device and a display;
   b. means for storing information relating to the potentially insurable risk in the first data base;
   c. automated means for evaluating the information stored in the first data base and for identifying additional elements of information required for evaluating the potentially insurable risk, and for requesting entry of said additional information for subsequent storage in the first data base;
   d. means for correlating selected elements of information from the first data base with corresponding elements of information previously stored in the second data base;
   e. means for assigning a weight to at least one of the selected elements of information from the first data base on the basis of predetermined relationships existing between the elements of information in the first data base and corresponding elements of information in the second data base;
   f. means for displaying information from the second data base, corresponding to at least one of the selected elements of information from the first data base, for use in assigning a weight to said element of information, means for monitoring an input device for entry of said weight, and means for storing said weight following entry thereof; and
   g. means for determining at least one risk classification for the potentially insurable risk from the weights assigned to the elements of information in the first data base.

2. Information processing apparatus according to claim 1, further comprising a plurality of expert modules, means for identifying an expert module corresponding to an element of information from the first data base for use in assigning a weight to said element of information, means for monitoring the input device for entry of said weight, and means for storing said weight following entry thereof.

3. Information processing apparatus according to claim 2, further comprising means for identifying an element of information in the first data base for which no corresponding information in the second data base exists and for which no expert module exists, and for selectively providing an option to assign a weight to said element of information.

4. Information processing apparatus according to claim 2, further comprising means for overriding the expert module, and for assigning a different weight to the corresponding element of information from the first data base.

5. Information processing apparatus according to claim 2, further comprising means for storing at least one statistical profile relating to a selected element of information from the first data base, and means for adjusting the weight assigned to at least one of said elements of information on the basis of said statistical profile.

6. Information processing apparatus according to claim 2, wherein said means for determining at least one risk classification includes means for combining the weights assigned to the elements of information in the first data base to derive a single weight representative of the potentially insurable risk.

7. Information processing apparatus according to claim 6, further comprising means for comparing the single weight representative of the potentially insurable risk to a standard for a risk of the same class.

8. Information processing apparatus according to claim 7, further comprising plan conversion means for determining the risk classification of the potentially insurable risk on the basis of the comparison of the single weight to the standard.

9. Information processing apparatus according to claim 2, further comprising means for quantitatively determining an expected profit resulting from a decision concerning the insurability of the potentially insurable risk according to the previously determined risk classification.

10. Information processing apparatus according to claim 9, further comprising means for storing information, including statistical data from previous transactions of a similar type, relating to the decision, means for determining a probability of generating the expected profit on the basis of said information, and means for further evaluating the expected profit in view of said probability.

11. Information processing apparatus according to claim 9, further comprising means for selectively changing the risk classification and for determining the impact of the change on the expected profit.

12. Information processing apparatus according to claim 1, further comprising:
   means providing a user data base;
   means for storing information relating to a plurality of apparatus users in the user data base;
   means for selecting one of said plurality of users on the basis of information stored in the user data base; and
   means for identifying the potentially insurable risk to be evaluated with the selected user.

13. Information processing apparatus according to claim 12, wherein said information stored in the user data base includes information relating to at least one of:
   a level of training of selected user;
   a level of experience of a selected user;
   a workload of a selected user; and
   at least one of a plurality of marketing factors.

14. Information processing apparatus according to claim 1, further comprising:
   means providing an installation specific data base;
   means for storing installation specific information relating to the potentially insurable risk in the installation specific data base;
   means for correlating selected elements of information in the first data base with corresponding elements of information in the installation specific data base; and
   means for assigning weights to said elements of information in the first data base on the basis of the information stored in the installation specific data base.

15. Information processing apparatus according to claim 1, further comprising:
   means providing a management information data base; and
   means for storing information relating to determination of the risk classification for the potentially insurable risk in the management information data base.

16. Information processing apparatus according to claim 1, further comprising:
   means for displaying selected elements of information from the first data base;
   means for monitoring an input device for changes and additions to the information in the first data base entered in response to the display; and
   means for storing said changes and additions in the first data base.

17. Information processing apparatus according to claim 1, wherein said means for displaying information from the second data base includes:
   means for determining if the identified element of information from the first data base is mentioned in the second data base;
   means for classifying the identified element of information into one of a plurality of categories;
   means for identifying elements of information from the second data base which correspond to the category into which the identified element of information from the first data base has been classified;
   means for determining a most appropriate match between the identified element of information and the elements of information from the second data base which correspond to the category in which the identified element of information from the first data base has been classified; and
   means for displaying said matching elements of information from the second data base for use in assigning a weight to the identified element of information from the first data base.

18. Information processing apparatus according to claim 1, wherein said means for storing information relating to the potentially insurable risk in the first data base, and said automated means for evaluating the information stored in the first data base and identifying additional elements of information required for evaluating the potentially insurable risk comprise a non-interactive portion of the apparatus; and, wherein said means for displaying information from the second data base for use in assigning a weight to an element of information, said means for monitoring an input device for entry of said weight, and said means for storing said weight following entry thereof comprise an interactive portion of the apparatus.

19. Information processing apparatus according to claim 18, wherein said non-interactive portion of the apparatus further comprises means for assigning a weight to at least one of the selected elements of information from the first data base on the basis of predetermined relationships existing between the elements of information in the first data base and corresponding elements of information in the second data base.

20. Information processing apparatus according to claim 18, wherein said information processing apparatus further comprises a user data base, and wherein the non-interactive portion of the apparatus further comprises means for selecting one of a plurality of users from the user data base, and identifying the potentially insurable risk to be evaluated with the selected user.

21. Information processing apparatus according to claim 19, wherein the interactive portion of the apparatus further comprises means for providing the selected user with an option to do at least one of the following:
   (a) examine or update the information in the first data base;
   (b) review the information stored in the second data base; and
   (c) proceed with the evaluation of the potentially insurable risk.

22. In an information processing apparatus having first and second data bases, an input device, and a display, a method for evaluating the insurability of a potentially insurable risk, comprising the steps of:
   a. storing information relating to the potentially insurable risk in the first data base;
   b. evaluating the information stored in the first data base by automated means to identify additional elements of information, based on said evaluation, required for evaluating the potentially insurable risk, and requesting entry of said additional information for subsequent storage in the first data base;
   c. correlating selected elements of information from the first data base with corresponding elements of information previously stored in the second data base;
   d. assigning a weight to at least one of the selected elements of information from the first data base on the basis of predetermined relationships existing between the elements of information in the first data base and corresponding elements of information in the second data base;

e. displaying information from the second data base, corresponding to at least one of the selected elements of information from the first data base, for use in assigning a weight to said element of information, monitoring an input device for entry of said weight, and storing said weight following entry thereof; and f. means for determining at least one risk classification for the potentially insurable risk from the weights assigned to the elements of information in the first data base.

23. The method of claim 22, wherein the information processing apparatus further comprises a plurality of expert modules, and wherein the method further comprises identifying an expert module corresponding to an element of information from the first data base for use in assigning a weight to said element of information, monitoring the input device for entry of said weight, and storing said weight following entry thereof.

24. The method of claim 23, comprising the additional step of identifying an element of information in the first data base for which no corresponding information in the second data base exists and for which no expert module exists, and selectively providing an option to assign a weight to said element of information.

25. The method of claim 23, comprising the additional step of overriding the identified expert module and assigning a different weight to the corresponding element of information from the first data base.

26. The method of claim 23, comprising the additional steps of storing at least one statistical profile relating to a selected element of information from the first data base, and adjusting one or more of the weights assigned to the elements of information from the first data base on the basis of said statistical profile.

27. The method of claim 23, wherein said step of determining at least one risk classification includes combining the weights assigned to the elements of information in the first data base to derive a single weight representative of the potentially insurable risk.

28. The method of claim 27, comprising the additional step of comparing the single weight representative of the potentially insurable risk to a standard for a risk of the same class.

29. The method of claim 28, comprising the additional step of determining the risk classification of the potentially insurable risk by comparing the single weight to the standard.

30. The method of claim 23, comprising the additional step of quantitatively determining an expected profit resulting from a decision concerning the insurability of the potentially insurable risk according to the previously determined risk classification.

31. The method of claim 30, comprising the additional steps of storing information, including statistical data from previous transactions of a similar type, relating to the decision, determining a probability of generating the expected profit on the basis of said information, and further evaluating the expected profit in view of said probability.

32. The method of claim 30, comprising the additional step of selectively changing the risk classification and determining the impact of the change on the expected profit.

33. The method of claim 23, wherein said information processing apparatus further comprises a user data base, and wherein the method comprises the additional steps of:

storing information relating to a plurality of apparatus users in the user data base;

selecting one of said plurality of users on the basis of information stored in the user data base; and identifying the potentially insurable risk to be evaluated with the selected user.

34. The method of claim 33, wherein said information stored in the user data base includes information relating to at least one of:

a level of training of a selected user;

a level of experience of a selected user;

a workload of a selected user; and at least one of a plurality of marketing factors.

35. The method of claim 23, wherein said information processing apparatus further comprises an installation specific data base, and wherein the method comprises the additional steps of:

storing installation specific information relating to the potentially insurable risk in the installation specific data base;

correlating selected elements of information in the first data base with corresponding elements of information in the installation specific data base; and assigning weights to said elements of information in the first data base on the basis of the information stored in the installation specific data base.

36. The method of claim 23, wherein the information processing apparatus further comprises a management information data base, and wherein the method comprises the additional step of storing information relating to determination of the risk classification for the potentially insurable risk in the management information data base.

37. The method of claim 23, comprising the additional steps of:

displaying selected elements of information from the first data base;

monitoring an input device for any changes and additions to the information in the first data base entered in response to the display; and storing said changes and additions in the first data base.

38. The method of claim 23, wherein said step of displaying information from the second data base includes:

determining if the identified element of information from the first data base is mentioned in the said data base;

classifying the identified element of information into one of a plurality of categories;

identifying elements of information from the second data base which correspond to the category into which the identified element of information from the first data base has been classified;

determining a most appropriate match between the identified element of information and the elements of information from the second data base which correspond to the category in which the identified element of information from the first data base has been classified; and means for displaying said matching elements of information from the second data base for use in assigning a weight to the identified element of information from the first data base.

39. The method of claim 22, wherein said method comprises:
- a non-interactive mode including at least the steps of storing information relating to the potentially insurable risk in the first data base, and evaluating the information stored in the first data base to identify additional elements of information required for evaluating the potentially insurable risk, and requesting entry of such information for subsequent storage in the first data base; and
- an interactive mode including at least the steps of displaying information from the second data base, corresponding to at least one of the selected elements of information from the first data base, for use in assigning a weight to said element of information, monitoring an input device for entry of said weight, and storing said weight following entry thereof.

40. The method of claim 39, wherein said non-interactive mode further includes the step of assigning a weight to at least one of the selected elements of information from the first data base on the basis of predetermined relationships existing between the elements of information in the first data base and corresponding elements of information in the second data base.

41. The method of claim 39, wherein said information processing apparatus further comprises a user data base, and wherein the non-interactive mode of the method comprises the additional steps of selecting one of a plurality of users from the user data base, and identifying the potentially insurable risk to be evaluated with the selected user.

42. The method of claim 41, wherein the interactive mode of the method comprises the additional step of providing the selected user with an option, upon entry to the interactive mode, to do at least one of the following:
   (a) examine or update the information in the first data base;
   (b) review the information stored in the second data base; and
   (c) proceed with the evaluation of the potentially insurable risk.

* * * * *